(12) United States Patent
Tateishi

(10) Patent No.: US 8,900,458 B2
(45) Date of Patent: Dec. 2, 2014

(54) METHOD OF ISOLATING TARGET SUBSTANCE USING MEMBRANE AND APPARATUS THEREFOR

(75) Inventor: Yasuhiro Tateishi, Tokyo (JP)

(73) Assignee: Tsukishima Kankyo Engineering Ltd., Tokyo (JP)

(*) Notice: Subject to any disclaimer, the term of this patent is extended or adjusted under 35 U.S.C. 154(b) by 1112 days.

(21) Appl. No.: 12/531,993

(22) PCT Filed: Mar. 19, 2008

(86) PCT No.: PCT/JP2008/055081
§ 371 (c)(1),
(2), (4) Date: Sep. 18, 2009

(87) PCT Pub. No.: WO2008/123099
PCT Pub. Date: Oct. 16, 2008

(65) Prior Publication Data
US 2010/0101997 A1    Apr. 29, 2010

(30) Foreign Application Priority Data
Mar. 22, 2007   (JP) ............... P2007-075655

(51) Int. Cl.
*B01D 61/00* (2006.01)
*C02F 1/44* (2006.01)
(Continued)

(52) U.S. Cl.
CPC ........ *B01D 61/027* (2013.01); *B01D 2317/022* (2013.01); *B01D 61/145* (2013.01); *B01D 2315/12* (2013.01); *B01D 61/12* (2013.01); *C07B 63/00* (2013.01); *B01D 2315/16* (2013.01); *B01D 61/22* (2013.01); *C07C 41/36* (2013.01); *B01D 65/02* (2013.01)
USPC ........... 210/651; 210/636; 210/637; 210/650; 210/652; 210/321.65; 210/106

(58) Field of Classification Search
None
See application file for complete search history.

(56) References Cited

U.S. PATENT DOCUMENTS 2,860,091 A    11/1958 Rosenberg
4,865,744 A *   9/1989 Hartling et al. ............... 210/651
(Continued)

FOREIGN PATENT DOCUMENTS

DE    19938874    2/2001
EP    0358255     3/1990
(Continued)

OTHER PUBLICATIONS
Frank Lipnizki et al., "Concepts of Industrial-Scale Diafiltration Systems", Desalination, 144 (2002), pp. 179-184.
(Continued)

Primary Examiner — Dirk Bass
(74) Attorney, Agent, or Firm — Hoffmann & Baron, LLP

(57) ABSTRACT

A separation apparatus using a membrane for diafiltration, which provides precise fractionation of a target substance by monitoring and regulating permeability of the target substance based on measurement values and analytical values indicating separation status, such as physical values and concentration of a permeate liquid, a circulating liquid and an internal circulating liquid in a membrane device. A diafiltration process including adding a cleaning liquid to an treating liquid which contains multiple target substances and extracting a target substance into the permeate liquid supplied from a membrane separation apparatus to fractionate the target substance from other target substances remaining in a residual liquid. In the present invention, permeability of the target substance is controlled by regulating or controlling at least one operating parameter, such as a flow rate of the permeate liquid, operating pressure and temperature of the membrane separation apparatus, and concentration and amount of a circulating liquid, to a predetermined range based on a separation status index and/or a progress index of a separating operation.

13 Claims, 18 Drawing Sheets

(51) Int. Cl.
*B01D 61/14* (2006.01)
*B01D 61/12* (2006.01)
*C07B 63/00* (2006.01)
*B01D 61/02* (2006.01)
*B01D 61/22* (2006.01)
*C07C 41/36* (2006.01)
*B01D 65/02* (2006.01)

(56) References Cited

U.S. PATENT DOCUMENTS

| 5,242,597 | A | 9/1993 | McArdle | |
|---|---|---|---|---|
| 2007/0049775 | A1* | 3/2007 | Endo et al. | 568/675 |

FOREIGN PATENT DOCUMENTS

| JP | 05-117196 | 5/1993 |
|---|---|---|
| JP | 10-211423 | 8/1998 |
| JP | 11-215980 | 8/1999 |
| JP | 2000317273 | 11/2000 |
| JP | 2001-500734 | 1/2001 |
| JP | 2001-232158 | 8/2001 |
| JP | 2001-259374 | 9/2001 |
| JP | 2001-525177 | 12/2001 |
| JP | 2002112800 | 4/2002 |
| JP | 2003-504638 | 2/2003 |
| JP | 2003-259900 | 9/2003 |
| JP | 2004-017035 | 1/2004 |
| JP | 2004-121961 | 4/2004 |
| JP | 2005-65541 | 3/2005 |
| JP | 2005-102519 | 4/2005 |
| JP | 3717193 | 9/2005 |
| JP | 3717193 | 11/2005 |
| WO | WO 98/12209 | 3/1998 |
| WO | WO 99/28490 | 6/1999 |
| WO | WO 01/06233 | 1/2001 |
| WO | WO2005077208 | 8/2005 |
| WO | WO2007120449 | 10/2007 |

OTHER PUBLICATIONS

Athanasios K. Goulas et al., "Purification of Oligosaccharides by Nanofiltration", Journal of Membrane Science, vol. 209, Issue 1, (2002), pp. 321-335.

Frank Lipinzki et al., "Concepts of Industrial-Scale Diafiltration Systems", *Desalination*, 144 (2002), pp. 179-184.

H. Oya et al., "Food Membrane Technology: Guidance to Membrane Technology", *Korin Publishing Co., Ltd.*, Tokyo, (1999), 9th issue, p. 25 and 32.

S. Nakao et al., "Analysis of Solutes Rejection in Ultrafiltration", *Journal of Chemical Engineering of Japan*, vol. 14, No. 1 (1981), pp. 32-37.

Athanasois K. Goulas et al., "Purification of Oligosaccharides by Nanofiltration", *Journal of Membrane Science*, vol. 209, Issue 1, (2002), pp. 321-335.

* cited by examiner

METHOD OF ISOLATING TARGET SUBSTANCE USING MEMBRANE AND APPARATUS THEREFOR

BACKGROUND OF THE INVENTION

1. Field of the Invention

The present invention relates to a method and apparatus for separating a liquid into a permeate liquid and a residual liquid (i.e., a non-permeate liquid) using a membrane. In particular, the invention relates to a method and apparatus for isolating and recovering, using a membrane, target substances including valuable substances and impurities, such as salts and the like, contained in a liquid to be processed. Such a process is widely conducted in, for example, the fermentation industry, the pharmaceutical industry, the sugar refining industry, the amino acid industry, the food industry, the dye industry, the pigment industry, the chemical industry, the metal refining industry and the waste-disposal industry. Materials to be treated may be in a liquid or solid state. More particularly, in separation, removal and refinement of target substances in an treating liquid, the present invention relates to a method and apparatus for efficiently separating and recovering target substances from various liquids to be treated containing target substances in a combined process of contacting the liquids to be treated with, for example, a cleaning liquid or an extraction liquid and membrane separation.

In addition, the present invention relates to a method and apparatus for separating target substances having closely similar permeability using a separation membrane by achieving permeability desirable for separation with a selected separation membrane through management and control of separating processes and a membrane separation apparatus for effective demonstration of separating capability of the used separation membrane.

This application claims priority of Japanese Patent Application No. 2007-75655 filed Mar. 22, 2007, which is incorporated herein by reference.

The aforementioned present method of separating target substances using a membrane may be applied to refinement of polyglycerins, which are usually petrochemically-derived or oleochemically-derived. Polyglycerins exist in many forms, including a mixture of low polymerization polyglycerins, such as diglycerin and triglycerin, a mixture of higher polymerization polyglycerins and a mixture of cyclic polyglycerins and by-products. Attempts have been made to increase or decrease the proportion of specific components in the mixture, in addition, to fractionate the specific components. The fractionation and refinement methods using polyglycerin for this purpose are identified by molecular distillation purification, distillation under reduced pressure using a steam career and simulated moving bed chromatography and the like (for example, Patent Document 7).

2. Background Art

In the past, diafiltration (also referred to as "diawash") using a membrane has been used in, for example, desalination of produced chemical dye and sugar refinement and is discussed in the references below.

For example, Patent Document 1 discloses a method of producing oligo syrup in which disaccharides, trisaccharides and even larger saccharides are obtained and a permeate liquid produced at a nanofiltration step is re-circulated. And describes a diafiltration process through nanofiltration that "in an aspect of the present invention, diafiltration also includes a nanofiltration step, in which water is added to a supply flow in a preferable amount corresponding to that of penetrant" (Patent Document [0036]).

Attempts have been made for effective diafiltration by selecting membranes according to target substances and operating a membrane device. For example, Patent Document 1 discloses, in Example 2 and Table 7, a result of a test that was "conducted in order to demonstrate the effects of changing the parameters on the filtering capability" (Patent Document, [0059] to [0064]).

In addition, A relationship between composition of a circulating liquid and composition of a permeate liquid in a membrane device has been presented as (for example, Non-Patent Document 3, Non-Patent Document 4).

Patent Document 1 also discloses, in Example 3 and Table 8, that "the results obtained on the penetrant (i.e., the permeate liquid) clearly demonstrate the influence of variation in the operating condition of the membrane separation apparatus. The obtained different flow rates of membrane permeation have provided different membrane selectivity for two compounds. All of the results demonstrate that the separation process may be changed and regulated". Description, however, on a method of controlling selectivity (i.e., permeability) of target substances is not given (Patent Document 1[0064]).

In addition, in order to detect an end point of a diafiltration process using a membrane, measurement values have been used as indices. Patent Document 2 discloses "enzymatic decomposition of carbohydrate in protein fractionation." Example 2 includes a description that "in order to fractionate carbohydrates and salts out of a protein extract, centrifugal supernatant is subject to ultrafiltration. The supernatant is concentrated to up to 5.5% DS and deionized water is added to the concentrated supernatant, which is then subject to diafiltration until the equation is satisfied: [permeate liquid (% DS)]/[residual liquid (% DS)]=0.09.".

Although the disclosed process is not applied to control of permeability of target substances using a membrane, a method of providing an end point of a diafiltration process in terms of % DS, which is a measurement value (Patent Document 2).

In addition, attempts have been made to control extensive bioprocesses using analytical values. For example, Patent Document 3 discloses application to diafiltration using an ultrafiltration membrane and includes a description that "in the patent document regarding monitoring and control of a real time in situ biomanufacturing process in accordance with infrared spectroscopy, process monitoring and control using infrared spectroscopy in a refinement stage of biomanufacturing" is disclosed. (for example, Patent Document 3[0064] [0117]).

Furthermore, various process concepts of diafiltration have been variously studied. For example, the present applicant has disclosed a method using time difference multistage counter-current and a method of "recovering, after the supply of the treating liquid is stopped, a target substance in the system through multistage counter-current washing and separating operations" (Patent Document 5 and 6). Furthermore, other references describe a wide variety of process concepts of industrial diafiltration. Diafiltration is segmented and described in terms of: (1) batch diafiltration; (2) continuous (multistage) diafiltration; and (3) (continuous multistage) counter-current diafiltration (for example, Patent Document 5, 6 and Non-Patent Document 1).

Another reference describes diffusion models and solute permeation coefficients (Non-Patent Document 2).

[Patent Document 1] Published Japanese translation No. 2001-525177

[Patent Document 2] Published Japanese translation No. 2001-500734

[Patent Document 3] Published Japanese translation No. 2003-504638

[Patent Document 4] Japanese Unexamined Patent Application No. H5-117196

[Patent Document 5] Japanese Unexamined Patent Application No. H10-211423

[Patent Document 6] Japanese Unexamined Patent Application No. 2004-17035

[Patent Document 7] Japanese Patent Publication No. 3717193

[Non-Patent Document 1] Concept of Industrial-scale Diafiltration Systems, Desalination 144 (2002) 179-184 Frank Lipnizki et al.

[Non-Patent Document 2] Haruhiko Oya and Atsuo Watanabe ed., "Food membrane technology: Guidance to membrane technology" Korin Publishing Co., Ltd., Tokyo, 1999, 9th issue, pages 25 and 32

[Non-Patent Document 3] Analysis of Solutes Rejection in Ultrafiltration, Journal of Chemical Engineering of Japan Vol. 14, No. 1 (1981) 32~37 Shin-ichi Nakao et al.

[Non-Patent Document 4] Purification of Oligosaccharides by Nanofiltration Journal of Membrane Science Vol. 209 Issue 1 (2002) 321~335 Athanasios K. Goulas et al.

DISCLOSURE OF THE INVENTION

Problems to be Solved by the Invention

However, most of commercially available nanomembranes and ultrafiltration membranes have indices to indicate capability of blocking substance in terms of, for example, molecular weight cut-off. Actual permeability, such as in terms of a molecular rejection, is, however, influenced by factors other than membrane types, such as usage history of a membrane, operating conditions, characteristics and composition of a supplied liquid and a circulating liquid to be used. And, although it is difficult to achieve a membrane that has separating capability to perfectly block one target molecule out of a target material and not to block other target molecules, it is desirable to develop a separation method utilizing a difference in permeability of target substances caused by a selected membrane by accurately selecting operating conditions.

The present invention has been made in view of the above circumstances, and an object thereof is to provide a novel method and apparatus for accurately fractionating a target substance by, during diafiltration using a membrane, monitoring and regulating permeability of a target substance using a measurement value and an analytical value representing separation status of a membrane device, such as concentration and physical values of a permeate liquid, a circulating liquid or an internal circulating liquid.

Means for Solving the Problem

To solve the aforementioned problem, an aspect of the present invention is a method of fractionating a target substance using a membrane, the method including: in a diafiltration process including supplying a membrane separation apparatus with an treating liquid containing multiple target substances and extracting a target substance into a permeate liquid supplied from the membrane separation apparatus to fractionate the target substance from other target substances remaining in a residual liquid, controlling permeability of the target substance by regulating or controlling at least one operating parameter to a predetermined range based on a separation status index and/or a progress index of a separating operation, the operating parameters including a flow rate of the permeate liquid, operating pressure and temperature of the membrane separation apparatus, and concentration and amount of a circulating liquid.

Also, in the method of fractionating a target substance described above, the separation status index or the operating parameter may be a flow rate of the permeate liquid in the membrane separation apparatus.

Also, in the method of fractionating a target substance described above, multiple or substantially successive stages of a series of diafiltration processes corresponding to the supply of the treating liquid may be provided, and permeability of the target substance may be controlled by provided predetermined ranges of the separation status index and/or the operating parameter suitably selected with respect to a progress index for each stage.

The predetermined ranges for the operating parameters and the separation status indices of "multiple or substantially successive stages" may be changed in a stepped or continuous manner. The predetermined ranges may also be changed in each of the stages. The corresponding predetermined values may be previously established in, for example, a table, may be obtained through calculation based on the operating parameters, the separation status indices, the progress indices, measurement values and analytical values from which these parameters and indices are derived, or based on other arbitrarily input data, or may be substantially continuously changed.

The separation status indices and the progress indices used for detecting a start and/or end point of each stage may be previously determined, may be selected from a table of a calculation equation or may be substantially continuously changed.

Also, in the aforementioned method of fractionating a target substance described above, the beginning and completion of each of the stages may be determined based on the separation status index and/or the progress index.

Also, in the method of fractionating a target substance described above, an amount of a liquid supplied to the membrane separation apparatus, an amount of a liquid extracted out of the system from the membrane separation apparatus or an amount of return liquid into the permeate liquid may be controlled based on an index substantially indicating concentration of the circulating liquid or the residual liquid processed in a separation membrane.

Note that any measurement values or analytical values may be used as the "measurement values substantially representing concentration" used as indices so long as they may be used as indices or original data with which the liquid concentration in the membrane device is properly controlled.

In a using multistage membrane separation apparatus manner, concentration may be controlled by, with concentration of the circulating liquid and the residual liquid in each membrane separation apparatus used as indices, substantially controlling a supplied liquid to the membrane separation apparatus, an extraction liquid from the membrane separation apparatus and a return liquid and controlling a supplied liquid, an extraction liquid and a return liquid from another membrane separation apparatus.

Note that the amount of the return liquid of the permeate liquid or the circulating liquid to the circulating liquid and the residual liquid is defined as "an amount of a liquid extracted from the membrane separation apparatus or its circulatory system to be returned. The extracted liquid to be returned may also be processed".

Also, in method of fractionating a target substance described above, the progress index may be at least one of an index indicating separation results in terms of an elapsed time, a cumulative amount of the permeate liquid, a cumulative amount of the supplied cleaning liquid, an amount of the circulation liquid, an amount of a liquid in the circulation tank, the residual liquid, the permeate liquid and concentration of the treating liquid, the degree Brix, the viscosity, the electric conductivity, a measurement value, the pH, an analytical value and a calculated value based on these indices and amounts.

Also, in the method of fractionating a target substance described above, the separation membrane may be a nanomembrane or an ultrafiltration membrane.

Also, in the method of fractionating a target substance described above, the separation membrane may be a tubular membrane.

Also, in the method of fractionating a target substance described above, the operating parameter may be the flow rate of the permeate liquid and the separation status index may be a degree Brix ratio which is a ratio of the degree Brix in the permeate liquid to degree Brix in the permeate liquid or to the degree Brix in the circulating liquid.

Also, in the method of fractionating a target substance described above, "a dilute liquid by extraction of a final circulating liquid of a previous batch process" and/or "a reprocessing liquid of a previous batch" and/or "a permeate liquid of a previous batch" may be used as an treating liquid, a cleaning liquid or a "recycling liquid" at a batch process subsequent to a batch process in which the liquids are produced.

Furthermore, in the method of fractionating a target substance using a membrane described above, the degree of progress of separation can be grasped to detect transition or end points of the stages quantitatively. Quantization may be conducted by using quantitative indices to be capable of being integrated or progress indices which are measurement values or analytical values indicating the separation results or calculated values obtained from the measurement values and the analytical values.

Also, in the method of fractionating a target substance using a membrane described above, one or more of a reverse osmosis membrane, a nanomembrane and an ultrafiltration (UF) membrane may be used in order to concentrate the target substance in the permeate liquid or the circulating liquid. Note that it suffices here that any (not all) of the target substances are to be concentrated.

Also, in the method of fractionating a target substance using a membrane described above, the treating liquid may be a mixture liquid containing polyglycerin.

Also, in the method of fractionating a target substance using a membrane described above, the treating liquid may be a mixture liquid containing multiple polyglycerins. At least one of glycerin, diglycerin and triglycerin can be removed from the mixture liquid. A mechanism for supplying the treating liquid may be a mechanism for receiving the treating liquid in the circulation tank.

Furthermore, in evaluation of a pressure-driven separation membrane or a membrane separation apparatus incorporating the same, substances or components to be processed in membrane separation, a membrane separation apparatus incorporating the same, the separation membrane or the membrane separation apparatus incorporating the same, and a solvent used therefor, the method of fractionating a target substance using a membrane according to the present invention may be applied as a method of evaluating the separation membrane. The evaluation method can utilizes a relationship between an index representing permeability, such as in terms of transmittance or a rejection of each substance or component in the mixture, and an index representing permeability, such as in terms of transmittance or a rejection of an arbitrarily selected substance or component.

Effects of the Invention

According to the present invention, a diafiltration process can be provided in which permeability of a target substance is controlled, thereby enabling precise fractionation of substances having closely similar permeability through membrane separation.

Also, according to the present invention, since the substances having closely similar permeability may be accurately separated from each other through membrane separation which can be operated at low temperatures, separation can be conducted in a condition where thermal decomposition or thermal alteration hardly occurs. A simple separation process which requires no additives or disposals during membrane separation can be provided.

According to the present invention, the target substances can be desirably separated into the permeate liquid and the residual liquid quickly by controlling a flow rate of the permeate liquid or permeation flux as the operating parameters.

According to the present invention, permeability of the membrane suitable for the status of the liquid to be processed or the degree of progress of separation can be controlled or regulated by applying a series of diafiltration processes corresponding to the supply of the treating liquid in multiple or substantially successive stages. In this manner, "precise fractionation" in which substances having closely similar permeability are separated from each other can be provided.

According to the present invention, the diafiltration process in which controlling concentration of the circulating liquid and the residual liquid processed in the separation membrane provides stable measurement values and analytical values of concentration of the permeate liquid or the circulating liquid regarding the amount of the liquid to be supplied to the membrane separation apparatus and the return amount of the permeate liquid and the residual liquid. In this manner, efficient diafiltration can be conducted with the circulating liquid having a stable concentration.

Also, according to the present invention, change in composition of the material to be treated in separation or change in condition of a separation membrane may be addressed. Composition of the residual liquid or composition of the permeate liquid after separation may be stabilized even if reproducibility of the separation conditions varies within tolerance. As a result, acquiring homogeneity of permeate liquid and residual liquid can be secured for diafiltration in a separation process based on the above-described operating parameters, separation status indices, progress indices or combination thereof.

Furthermore, according to According to the present invention, precise fractionation using a nanomembrane or an ultrafiltration membrane can be conducted.

Also, Target substances which have not been recovered as a permeate liquid or a residual liquid in a previous cycle may be recovered in the subsequent cycle as the permeate liquid or the residual liquid. In this manner, a recovery rate of the substances increases to able to prevent occurrence of unnecessary waste.

If a material to be processed includes salts, such as sodium chloride, sodium chloride may be removed along with low-molecular glycerin and polyglycerin and the residual liquid can be recovered containing polyglycerin with a reduced amount of salts, such as sodium chloride. The membrane can be selected from a nanomembrane and an ultrafiltration membrane according to purpose.

According to the present invention, if the treating liquid is polyglycerin, the treating liquid can be refined by causing low molecular weight materials to permeate through a nanofiltration membrane, an ultrafiltration membrane or a reverse osmosis membrane so as to remove polyglycerin.

Also, according to the present invention, diglycerin can be removed from a mixture liquid containing an treating liquid having multiple polyglycerins. In particular, a mixture liquid containing polyglycerins may be refined to remove glycerin, diglycerin and triglycerin.

Furthermore, concentration of highly hydrophobic material in a mixture liquid containing polyglycerin can be to being reduced. A product obtained through refinement may be used as a material of polyglycerin fatty acid ester.

DESCRIPTION OF REFERENCE NUMERALS

Figure 1:
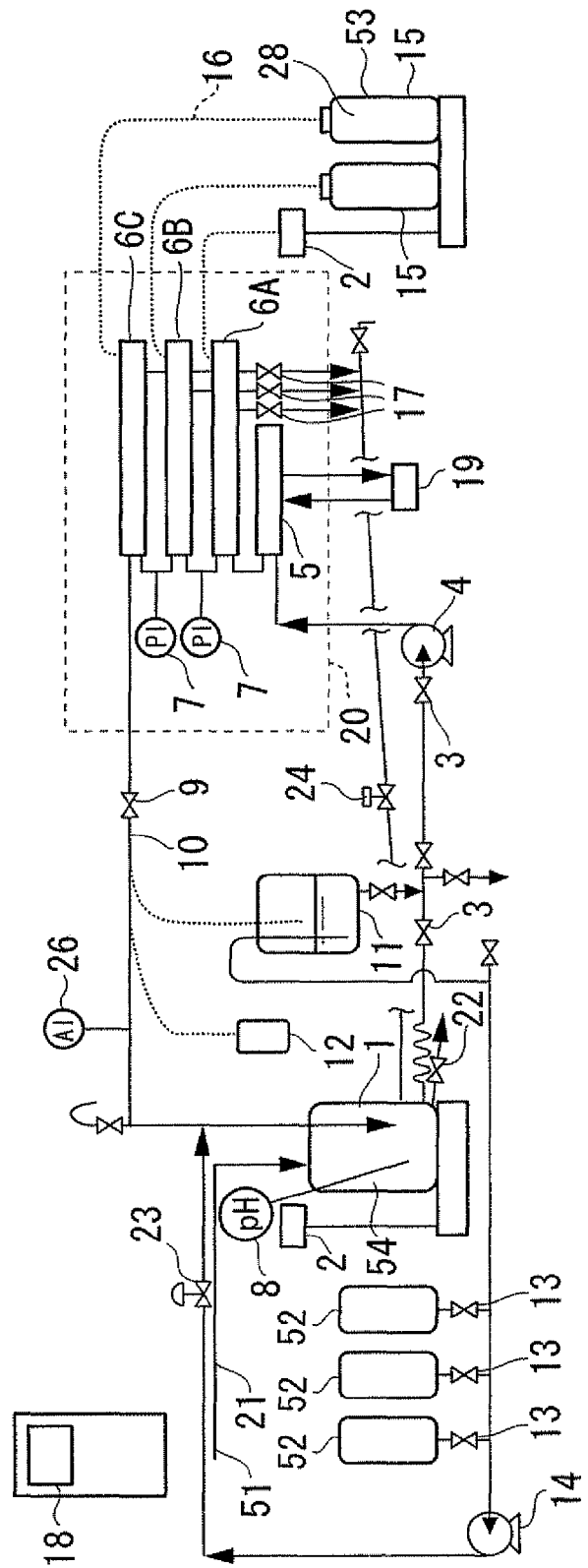
FIG. 1 is an exemplary flowsheet of a batch diafiltration process.

1: circulating liquid tank, 2: scale, 3: inlet pipe for pressure increase pump, 4: pressure increase pump, 5: heat exchanger, 6a: membrane module A, 6b: membrane module B, 6c: membrane module C, 7: pressure meter, 8: ph meter, 9: pressure control valve, 10: circulating liquid discharge pipe/hose, 11: container for circulating warm cleaning liquid for membrane, 12: container for extracted circulating liquid 13: cleaning liquid storage tank, 14: cleaning liquid pump, 15: permeate liquid container, 16: pipe/hose for permeate liquid, 17: permeate liquid drain hose 18: control panel, 19: chiller water unit, 20: membrane separation apparatus, 21: mechanism for supplying treating liquid, 22: mechanism for extracting circulating liquid, 23: mechanism for supplying cleaning liquid, 24: mechanism for extracting permeate liquid 25: mechanism for measuring flow rate of the permeate liquid, 26: mechanism for measuring concentration of circulating liquid, 27: mechanism for maintaining concentration of circulating liquid by controlling amount of cleaning liquid to be supplied, 28: mechanism for measuring concentration of permeate liquid, 29: mechanism for maintaining temperature of circulating liquid, 30: mechanism for regulating return amount of permeate liquid to circulating liquid, 31: previous batch storage tank 32: internal circulation pump, 33: cleaning liquid regulating valve, 51: treating liquid 52: cleaning liquid, 53: permeate liquid, 54: residual liquid, 55: return permeate liquid, 100: permeate liquid flow meter, 101: pressure meter, 130: flow control valve 135: flow control valve, 140: flow control valve 145: pump, 150: flow control valve

DESCRIPTION OF THE PREFERRED EMBODIMENTS

Commercially available nanomembranes and ultrafiltration membranes have rough indices representing the capability of blocking a substance in terms of, for example, molecular weight cut-off. Actual permeability, such as in terms of a molecular rejection, is, however, influenced by various factors as described above. The present invention is a method and apparatus for providing desired separation by suitably controlling permeability of membrane separation apparatus for target substances.

Nanomembranes and ultrafiltration membranes are based on a principle of a "pressure-driven membrane process" in which a supplied liquid to the separation membrane or a circulating liquid is pressurized so that substances are extracted into the side of permeate liquid. The following facts are previously known and various theoretical studies have been made therefor. A flow rate of the permeate liquid is changed depending on the circulating liquid pressure. Higher pressure may increase the flow rate of the permeate liquid so as to improve a rejection of each substance. Lower pressure may usually decrease the flow rate of the permeate liquid so as to reduce the rejection.

Regarding the relationship between the transmittance of polyglycerin and the permeation flux, the inventors of the present invention of the present invention conducted a separation test using a membrane AFC30 and a mixture liquid of diglycerin (G2), triglycerin (G3), tetraglycerin (G4) and pentaglycerin (G5) at the temperature of 32 to 42° C. The result is shown in Tables 1, 2 and 3.

Test conditions shown in Table 1 will be described.

Test equipment: Membrane separation apparatus BRO/BUF manufactured by PCI Membranes (ITT PCI Membranes Ltd.) loaded with a membrane AFC30 in three 1.2 m B1 membrane modules.

Analyzing method: polyglycerin is analyzed in the following manner: a sample is dehydrated in a concentration device to provide a concentrated sample; an internal standard liquid is prepared by adding pyridine to tetradecane; to the concentrated sample, the internal standard liquid, hexamethyldisilazane, chloro methylsilane, chloro trimethylsilane and other substances are added and the obtained mixture is heated; and the obtained product is trimethylsilylated (TMS) and analyzed in gas chromatography.

Also, the test equipment is operated to conduct diafiltration. During the diafiltration process, a permeate liquid is taken out from a sampling port in a drain pipe of the B1 membrane module of the AFC30, and the flow rate of the permeate liquid at this time is recorded, and then samples of the circulating liquid and the permeate liquid at this time are analyzed.

Transmittance ([concentration of the component in the permeate liquid]/[concentration of the component in the circulating liquid]) is calculated based on the concentration of the circulating liquid given in Table 1 and the permeate liquid concentration given in Table 2. The transmittance G2, G3 and G4 result in a wide range of values and are 0.28 to 0.77, 0.07 to 0.33 and 0.02 to 0.07, respectively. A relationship between these values and the permeation flux is studied. Alphabet letters in the permeate liquid numbers, namely, A1, A2 and A3 . . . , given in Table 2 correspond to the used circulating liquid and numerical values correspond to the number of the three modules, namely, 1, 2 and 3, in this order from the upstream.

A transport equation in the separation membrane on a disliquid diffusion model is given in page 30 of the above-mentioned Non-Patent Document 2.

$$Rint=Jv/(Jv+Bav) \qquad \text{Equation 1-22}$$

wherein Rint represents a rejection (−), Jv represents the permeation flux (m/sec in the reference) and Bav represents a solute permeation coefficient (m/sec in the reference).

This equation 1-22 is transformed and the following equations are assumed:

$$Rint=Jv/(Jv+Bav)$$

$$1-Cp/Cm=Jv/(Jv+Bav).$$

Cm which is the concentration of the membrane surface here cannot be measured directly. Accordingly, in an analogy made by replacing the concentration Cm with Cb, concentration of circulating liquid of the processed liquid which may be measured directly, the following analogy equation is found for trial calculation with Cp/m being Cp/Cb=transmittance:

$$\therefore Cp/Cb=\text{Transmittance}=1-Jv/(Jv+B),$$

$$\therefore \text{Transmittance}=Bav/(Jv+Bav),$$

$$\therefore 1/\text{Transmittance}=1+Jv/Bav, \text{ which is simplified to}$$
$$1/\text{Transmittance}=1+Jx(1/B).$$

Wherein J represents the flux (kg/m$^2$/hr) and (1/B) represents a trial calculation coefficient. The trial calculation coefficient (1/B)=(1/Transmittance−1)/J, which is equivalent to the solute permeation coefficient, is obtained from the values of the transmittance and the flux obtained from the separation experiment of polyglycerin, which will be shown in Table 3.

As shown in Table 2, values of the permeation flux, and thus corresponding transmittance, are significantly different from each other among the AFC30 membranes loaded in the three membrane modules. The inversely calculated trial calculation coefficients (1/B) (see Table 3) have values close to each other for each of the circulating liquids. Especially the trial calculation coefficient (1/B) for triglycerin are close in value among the five circulating liquids. The inventors of the present invention have found that an operating method may be implemented to maintain or change the transmittance with respect to one component or other components by managing the flow rate of the permeate liquid or the permeation flux by changing operating pressure.

The data labeled with A, B, C, D and E in Table 2 are values of the concentration ratio from 1.0 to 0.33 of diglycerin to that of triglycerin in the circulating liquids in this order. High concentrate triglycerin tends to have the trial calculation coefficients shown in Table 3 are close in value among A, B, C, D and E. On the other hand, with the decrease in the ratio of concentration, permeability of other polyglycerins, such as diglycerin, becomes greater. This implies an influence of change in composition. Based on those knowledges, the inventors of the present invention have found a method of controlling separating capability using operating parameters, such as the flow rate of the permeate liquid, the operating pressure and temperature of the membrane separation apparatus, the concentration of the circulating liquid and the amount of the circulating liquid in accordance with the degree of progress in diafiltration.

$$1/\text{Transmittance}=1+Jv/Bav \qquad \text{Equation 1}$$

Assuming that the above equation is satisfied at the same time for two components, Jv is eliminated and an equation defining a relationship between each transmittance of two components will be considered below. In the equations below, PSG represents transmittance, PSGA represents component A and PSGB represents component B.

$$BavA(1/PSGA-1)=BavB(1/PSGB-1)$$

$$\therefore (1/PSGA-1)=(1/PSGB-1)/(BavA/BavB)$$

$$\therefore (1-PSGA)PSGA=(1-PSGB)/PSGB/(BavA/BavB)$$

Figure 2:
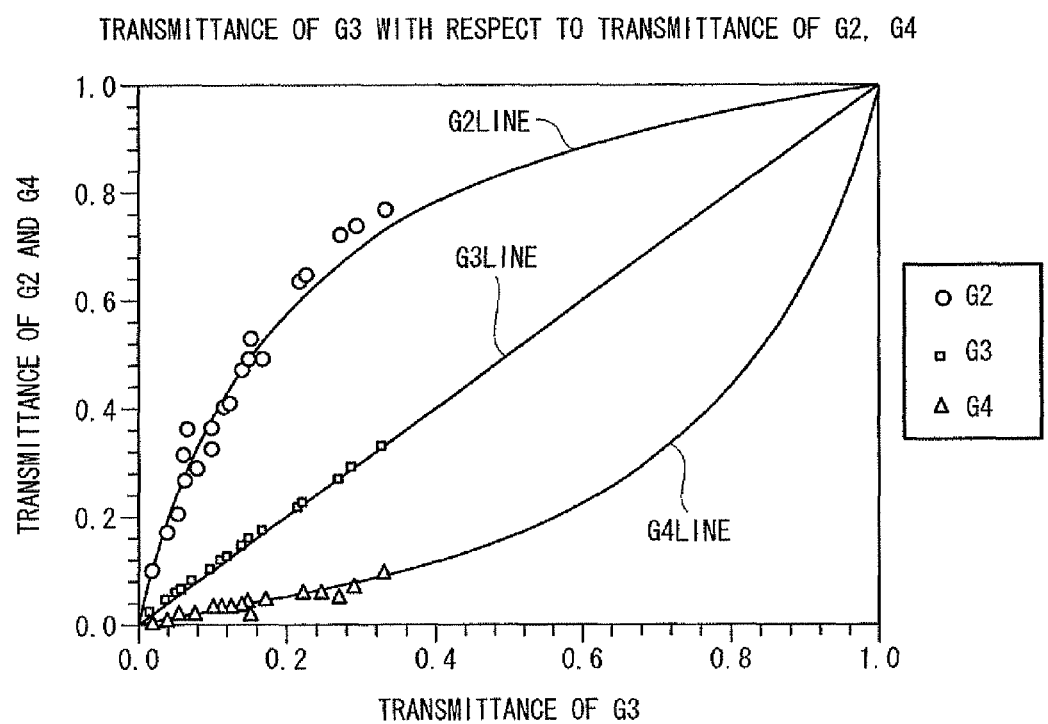
FIG. 2 shows is an exemplary view of a relationship among transmittance of triglycerin, transmittance of diglycerin and transmittance of tetraglycerin in a nanofiltration membrane.

In FIG. 2, transmittance of triglycerin (G3) shown in Table 2 is plotted along the horizontal axis and transmittance of diglycerin (G2), triglycerin (G3) and tetraglycerin (G4) in the circulating liquid and permeate liquid are plotted along vertical the axis. Two curves extending from the origin toward the point (1, 1) are virtual curves provided from trial calculation for each polyglycerin using the coefficient α in the equation below. These coefficients are obtained from an arithmetic average of BavGi/BavG3 at G2 and G4 calculated from the values of transmittance of Table 2.

$$(1-PsgGi)/PsgGi=(1-PsgG3)/PsgG3/\alpha Gi-G3 \qquad \text{Equation 2}$$

αG2−G3=5.53 if i=2 in the above equation,
αG4−G3=0.20 if i=4 in the above equation.

Since the relationships between G2 and G3 and between G4 and G3 of FIG. 2 are well applied to the above-described virtual curve, the inventors of the present invention have confirmed that the data in a mixed system of saccharide, disaccharides, trisaccharide and greater saccharides given in Table 7 of the Patent Document 1, the data in a single component liquid of Vitamin B$_{12}$, raffinose, sucrose, glucose and glycerin given in the above-mentioned "Analysis of solutes rejection in ultrafiltration," and the data in an oligosaccharide liquid given in the above-mentioned "Purification of oligosaccharides by nanofiltration" can be addressed in the same manner as in preferred Equation 2 above.

Figure 4:
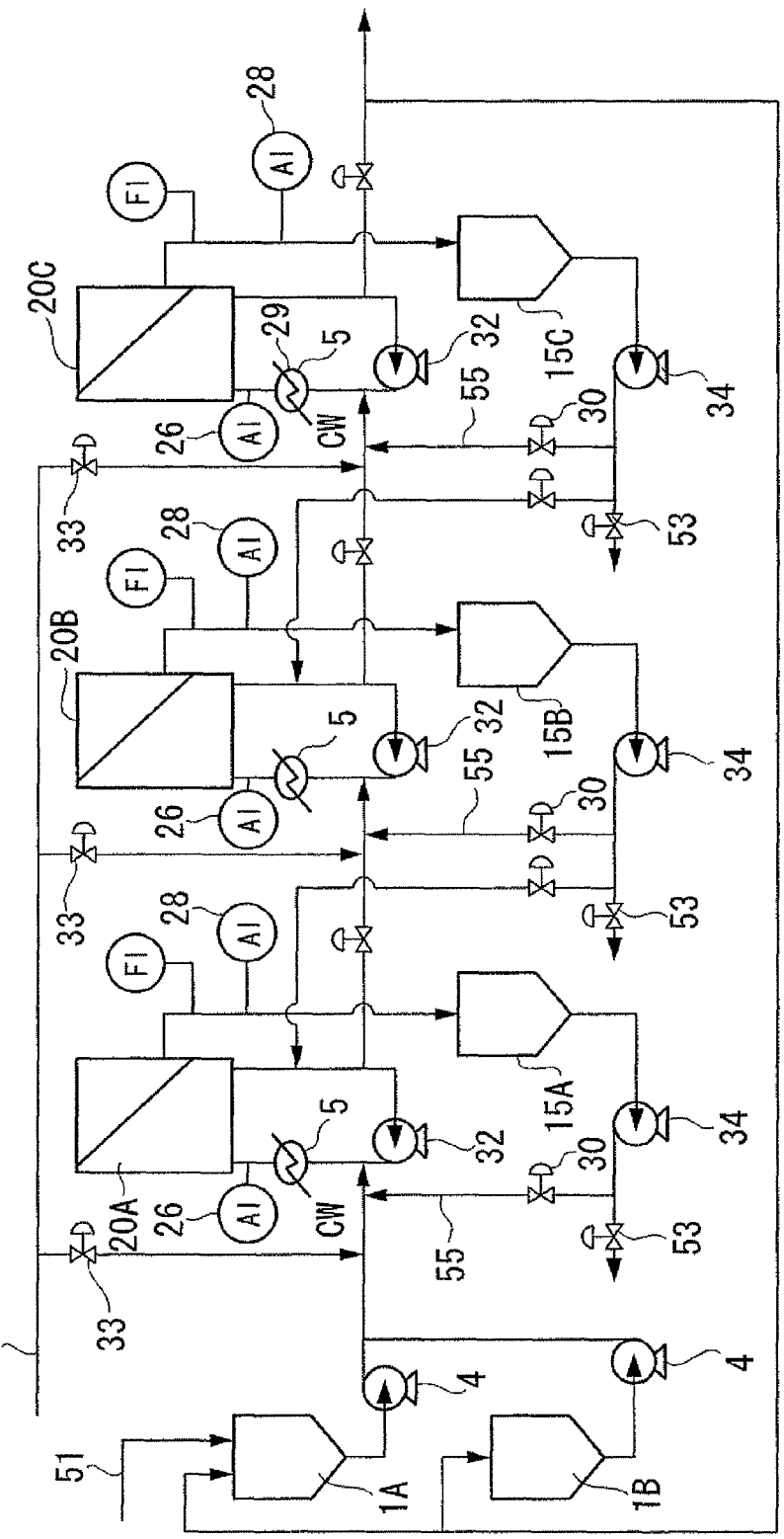
FIG. 4 illustrates a configuration of a continuous multi-stage diafiltration apparatus.

The data in an oligosaccharide liquid in a separation membrane DS-5-DL given in FIG. 4 of the above-mentioned "Purification of oligosaccharides by nanofiltration" may be appropriately applied to Equation 2 of this specification in relationships between the permeation flux and each transmittance of sucrose and fructose and between sucrose and raffinose. It has been also confirmed that, based on a graph having all the data, mutual relationships between transmittances of the components may be significantly represented by simple curves or straight lines from a logarithmic graph having vertical (fructose or raffinose) and horizontal (transmittance of sucrose) axes similar to those shown in FIG. 2.

tration using a membrane. Thereby, the inventors of the present invention have addressed problems involved in utilizing influence, on the permeability, of the operating parameters including the operating pressure, operating temperature, operation concentration and hydrogen-ion density (pH) in the membrane separation apparatus in order to provide an opera-

TABLE 1

| CIRCULATING LIQUID NO. | pH [-] | DEGREE BRIX | TOTAL ORGANIC MATERIAL [wt %] | INLET PRESSURE [Bar] | OUTLET PRESSURE [Bar] | CIRCULATING LIQUID TEMPERATURE [° C.] | CIRCULATING LIQUID wt % | | | | G2/G1 [-] |
|---|---|---|---|---|---|---|---|---|---|---|---|
| | | | | | | | G2 | G3 | G4 | G5 | |
| A | 4.16 | 20.6 | 23.2 | 29.5 | 26 | 41.5 | 10.0 | 10.0 | 1.8 | 0.5 | 1.00 |
| B | 4.21 | 18.1 | 20.2 | — | — | 37 | 6.5 | 9.8 | 2.2 | 0.6 | 0.67 |
| C | 4.3 | 16.9 | 19.8 | 36 | 33 | 42 | 5.0 | 10.8 | 2.3 | 0.6 | 0.47 |
| D | 4.49 | 12.7 | 13.7 | — | — | 32 | 2.0 | 7.7 | 2.3 | 0.7 | 0.26 |
| E | 4.57 | 13 | 14.4 | 28.5 | 26 | 32 | 2.7 | 8.1 | 2.1 | 0.6 | 0.33 |

TABLE 2

| PERMEATE LIQUID NO. | PERMEATION FLUX [kg/m2/hr] | pH [-] | DEGREE BRIX [%] | ORGANIC SUBSTANCE CONCENTRATION [wt %] | TRANSMITTANCE [-] | | | PERMEATE LIQUID CONCENTRATION [wt %] | | |
|---|---|---|---|---|---|---|---|---|---|---|
| | | | | | G2 | G3 | G4 | G2 | G3 | G4 |
| A1 | 14.4 | 4.33 | 8.3 | 9.0 | 0.649 | 0.225 | 0.061 | 6.51 | 2.26 | 0.11 |
| A2 | 11.5 | 4.30 | 9.5 | 10.6 | 0.740 | 0.290 | 0.070 | 7.42 | 2.92 | 0.13 |
| A3 | 9.6 | 4.30 | 10.5 | 11.4 | 0.773 | 0.328 | 0.096 | 7.75 | 3.30 | 0.17 |
| B1 | 17.7 | 4.41 | 5.1 | 5.1 | 0.492 | 0.170 | 0.045 | 3.23 | 1.66 | 0.10 |
| B2 | 13.8 | 4.40 | 3.2 | 6.5 | 0.640 | 0.219 | 0.043 | 4.19 | 2.13 | 0.09 |
| B3 | 10.4 | 4.36 | 7.3 | 7.6 | 0.721 | 0.271 | 0.055 | 4.72 | 2.64 | 0.12 |
| C1 | 29.9 | 4.69 | 2.6 | 2.9 | 0.327 | 0.098 | 0.027 | 1.64 | 1.05 | 0.06 |
| C2 | 24.5 | 4.62 | 3.1 | 3.5 | 0.408 | 0.122 | 0.029 | 2.04 | 1.31 | 0.07 |
| C3 | 19.2 | 4.57 | 4.0 | 4.4 | 0.528 | 0.154 | 0.019 | 2.65 | 1.65 | 0.04 |
| D1 | 37.9 | 5.00 | 1.2 | 1.2 | 0.282 | 0.073 | 0.015 | 0.57 | 0.56 | 0.04 |
| D2 | 29.5 | 4.94 | 1.5 | 1.6 | 0.359 | 0.100 | 0.026 | 0.73 | 0.77 | 0.06 |
| D3 | 24.0 | 4.86 | 2.1 | 2.3 | 0.488 | 0.149 | 0.040 | 0.99 | 1.15 | 0.09 |
| E1 | 33.6 | 4.96 | 1.2 | 1.3 | 0.266 | 0.066 | 0.015 | 0.71 | 0.54 | 0.03 |
| E2 | 25.9 | 4.94 | 1.4 | 1.5 | 0.293 | 0.079 | 0.020 | 0.78 | 0.64 | 0.04 |
| E3 | 17.9 | 4.82 | 1.9 | 2.1 | 0.405 | 0.112 | 0.027 | 1.08 | 0.91 | 0.06 |

*A, B, C, D and E: circulating liquid number

TABLE 3

| PERMEATE LIQUID NO. | TRIAL CALCULATION VALUE 1/B = (1/TRANSMITTANCE − 1)/ PERMEATION FLUX | | |
|---|---|---|---|
| | G2 | G3 | G4 |
| A1 | 0.038 | 0.239 | 1.074 |
| A2 | 0.031 | 0.213 | 1.153 |
| A3 | 0.031 | 0.213 | 0.986 |
| B1 | 0.058 | 0.276 | 1.207 |
| B2 | 0.041 | 0.258 | 1.598 |
| B3 | 0.037 | 0.259 | 1.646 |
| C1 | 0.069 | 0.308 | 1.225 |
| C2 | 0.059 | 0.294 | 1.383 |
| C3 | 0.047 | 0.287 | 2.691 |
| D1 | 0.067 | 0.334 | 1.683 |
| D2 | 0.061 | 0.306 | 1.248 |
| D3 | 0.044 | 0.237 | 1.000 |
| E1 | 0.082 | 0.422 | 1.946 |
| E2 | 0.093 | 0.453 | 1.928 |
| E3 | 0.082 | 0.444 | 1.993 |

It has been important for the inventors of the present invention to maintain permeability of the substances to suitable ranges in order to appropriately conduct separation of target substances having very similar permeability through diafiltration status suitable for promoting permeation of substances to be permeated and for controlling permeation of substances not to be permeated.

In Table 2, permeability in a condition with different temperatures, pressures and pHs is represented as transmittances. Regarding the transmittances of the permeate liquid in the conditions of all the circulating liquids of A, B, C and D, it is considered that the flow rate or the permeation flux has influence on the fact that the transmittance values differ among the circulating liquids from each of the modules.

In trial calculation of $1/B=(1/\text{Transmittance}-1)/J$ from the transmittance value of the permeate liquid obtained from each module in the circulating liquid of the conditions represented to Table 3 and the value of the flux at that time, the obtained results are substantially in agreement for G3 in each module of the circulating liquid and are closely similar in G2 and G4 at a comparative level with G3. Thereby, the inventors of the present invention have found that the separation permeability of membrane separation may be controlled by regulating the flow rate of the permeate liquid through regulation of pressure of the circulating liquid while managing parameters that may affect the circulating liquid temperature of the membrane separation apparatus, concentration of the circulating liquid, such as in terms of content organic materials, the flow rate of the permeate liquid, such as in terms of an amount of the circulating liquid and separativity. They also have recognized that this separativity may also be used (i.e., maintained or changed rapidly).

In the equations, "Transmittance" represents [concentration of target substance in permeate liquid]/[concentration of target substance in circulating liquid](−), J represents the permeation flux (kg/m²/hr) and B represents calculated value (kg/m²/hr).

In FIG. 2, transmittance of G3 in Table 2 is plotted along horizontal axis and transmittances of G2, G3 and G3 are plotted along vertical axis. Regarding the transmittances in different conditions as to permeation flux and temperature shown in Table 2 and 3, permeability for each single component in each data is different from each other. The transmittances of a basic component (G3 in FIG. 2) and other components (G2 and G4 in FIG. 2), however, are correlated to each other.

Also, the inventors of the present invention have assumed that the relationship depends on the membrane types. Accordingly, the inventors of the present invention have conceived to control separativity of membrane separation as the permeability of the entire substance group having a permeating property, and in particularly, conceived to control permeability of the entire substance group by regulating the flow rate of the permeate liquid.

The inventors of the present invention have focused on management of concentration of content material in the process liquid (i.e., the circulating liquid and the internal circulating liquid), and management of the permeate liquid through similar measurement of concentration. That is, the inventors of the present invention have conceived that the refining capability and operability using a membrane may be improved through management of the measurement values of concentration of the content materials in the supplied liquid to the membrane separation apparatus and the internal circulating liquid, and especially concentration of the circulating liquid, such as, in terms of degree Brix and density, and management of the measurement values from measuring devices and analyzing devices including a refractometer of the permeate liquid, a degree Brix meter and an electric conductivity meter. The management described above are conducted in parallel.

The present invention has been made based on the above knowledges and can desirable separation by using indices representing separation status and progress in a diafiltration process to set up operating parameters for managing progress and operation until the process is completed.

Next, terms used in the specification will be described.

Diafiltration

In the specification, diafiltration for membrane separation is defined as "an operation of separating target substances into a permeate liquid and a non-permeate liquid (i.e., a residual liquid and an internal circulating liquid) by adding a cleaning liquid to suspension, an treating liquid or a solution in process which are supplied as an object for membrane separation and removing the permeate liquid out of the membrane separation apparatus to obtain the residual liquid." Both of the substances to be extracted into the permeate liquid and the substances to be left in the residual liquid are referred to as the target substances. The cleaning liquid may be a fresh cleaning liquid and may be a liquid containing target substances, such as a permeate liquid, prepared in or separately from the process. Alternatively, the permeate liquid may be removed without addition of another cleaning liquid if the residual liquid or treating liquid is thin. These are all included in the definition of diafiltration.

Treating Liquid (Crude Liquid)

The "treating liquid" used for in the present invention may include various liquids of materials to be filtered, which may be in a liquid or solid state. The treating liquid contains a solvent, such as water, and target substances. A solvent in the treating liquid is a mixture of a water-soluble organic solvent, such as water and alcohol, and water or an organic solvent. Although the target substance may preferably be in a liquid state, they may be contained in a solid state, may be in a distributed liquid phase or may be contained in a distributed liquid phase. Also, the target substances include object substances to be separated, such as organic materials, inorganic materials, salts, reaction materials, products, by-products, valuable substances and harmful materials.

In many preferred cases, the concentration of content materials in the treating liquid is desirably close to uppermost limit it to be handled by the membrane separation apparatus. If the treating liquid is supplied in a diluted state, however, diafiltration may be conducted without addition of a cleaning liquid so as to extract target substances to the permeate liquid. Diafiltration may also be conducted after a concentrating process in the membrane separation apparatus. If a diluted liquid of the residue liquid at the time of transfer generated in a previously conducted batch process and the permeate liquid obtained in related processes are used as the treating liquid, such liquids may be concentrated in advance or in parallel with the diafiltration process using, for example, a separate membrane device. A solid content or an treating liquid may alternatively be diluted in advance with a cleaning liquid and a circulating liquid.

In the course of the membrane process, the treating liquid is treated as the "circulating liquid" or the "internal circulating liquid" in the processing unit, is left in the processing unit and extracted out of the system as the "residual liquid" with the progress of processing.

Solvent

A "solvent" used in the present invention is a liquid used for the handling of the treating liquid. The solvent may include a liquid of a water-soluble solvent, such as water, warm water, cold water and ethanol, organic solvents or mixtures thereof.

Membrane Cleaning Liquid

In order to clean the membrane using detergent or a solvent, a cleaning liquid for membrane cleaning is described as a membrane cleaning liquid.

Fresh Cleaning Liquid

A "fresh cleaning liquid" used in the present invention is a cleaning liquid supplied from outside of a system suitable for target separation. The fresh cleaning liquid may be water-soluble solvents, such as water, warm water, cold water, and ethanol water, or organic solvents, such as hexane. The fresh cleaning liquid is not necessarily one or more pure solvents or a mixture thereof, but may be suitable for the cleaning operation.

Cleaning Solution

A "cleaning liquid" used in the present invention may include any kind of fluids to be added to the treating liquid, the circulating liquid or the internal circulating liquid in the diafiltration process. That is, the liquid with which the apparatus is filled up before operation or the liquid supplied for cleaning in the diafiltration process is also included in the cleaning liquid. The fresh cleaning liquid, supplied from outside of the system, is also included in the cleaning liquid. The cleaning liquid also can be used as a solvent (i.e., an extracting agent) for extraction. Such a solvent is used as a permeate liquid for obtaining an extracting liquid from a material to be treated. That is, the cleaning liquid is added to the material to be filtered as an extracting liquid for extracting substances contained in a disperse phase in the material to be filtered. An extracting liquid is taken from the treating liquid with the target substances in the treating liquid as the permeate liquid from which substances blocked by the membrane are removed.

Separation Membrane

A "separation membrane" used in the present invention is also referred to simply as a "membrane," which may be a reverse osmosis membrane (RO membrane), a nanomembrane (nanofiltration membrane and NF membrane) or a pressure-driven ultrafiltration membrane (UF membrane). These membranes are loaded in tubular, spiral, hollow fiber, and flat film membrane modules, or in membrane separation apparatuses. The membrane has a function to separate a liquid to be processed supplied to a membrane separation apparatus into a permeate liquid and a non-permeate liquid (i.e., a residual liquid or a concentrate). A preferred membrane module is a tubular membrane because of its availability of uniform concentration distribution on a membrane surface. The membrane module, however, can be a spiral membrane, a hollow fiber, or a pressure-driven membrane, such as a flat membrane. The membrane can be made of organic materials, inorganic materials and a mixture thereof.

Membrane Separation Apparatus

A basic configuration of a "membrane separation apparatus" used in the present invention may be a suitably selected separation membrane, its membrane module or a aggregation of membrane modules. Is some cases, membrane separation apparatuses may further include an internal circulation pump, a heat exchanger and pipes connecting the same. A liquid to be processed, an treating liquid, a cleaning liquid, diawater and other liquids are supplied to the membrane separation apparatus after being pressurized by a pressure increase pump. These liquids may alternatively be pressurized in advance and introduced into the membrane separation apparatus through a flow control valve or a pressure control valve. Operating pressure in the membrane separation apparatus is controlled by a suitably selected pressure regulating mechanism, such as a control valve provided in an extraction pipe of the residual liquid discharged from the membrane module, and a regulating valve provided in a return pipe of the pressure increase pump. Also, the membrane separation apparatus may be provided with a unit for extracting the permeate liquid from the membrane module.

NF Membrane

The International Union of Pure and Applied Chemistry (IUPAC) defines a nanofiltration process as "a pressure-driven membrane separation process to block particles and polymers smaller than 2 nm." According to the IUPAC definition, a membrane used in the present invention for nanofiltration is referred to as a nanomembrane (nanofiltration membrane, NF membrane). Nanomembranes may include nanomembranes used in a water system and hydrophobic nanomembranes used exclusively for organic solvents.

NF membranes used in a water system may include, AFC80, AFC30 and AFC40 manufactured by PCI Membranes, Desal 5DL and Desal 51HL manufactured by Osmonics, and NTR7450 and manufactured by Nitto Denko Corp., and NF-2540 manufactured by FILMTEC. Examples of membranes used mainly in an organic solvent system can be represented as STARMEM (registered trademark) 120 and STARMEM (registered trademark) 240 manufactured by Davison Membranes.

UF Membrane

Similarly, IUPAC defines an ultrafiltration process as a "pressure-driven membrane separation process to block particles and polymers having a particle diameter of 0.1 to 2 nm." According to the IUPAC definition, a membrane used in the present invention for ultrafiltration is referred to as an ultrafiltration membrane (UF membrane). Examples of the UF membranes can be represented as CA202, EM006, ES006, ESP04, ES404, PU608, ES209, PU120, FPT03, FPA03, FP100, FPI20, FPA20, FP200 and L6000 manufactured by PCI Membranes.

RO Membrane

Similarly, IUPAC defines a reverse osmosis process as a "a pressure-driven separation process in a liquid phase to cause osmotic pressure difference and a selective movement of a solvent in a reverse direction when a membrane is pressurized at one side." According to the IUPAC definition, a membrane used in the present invention for reverse osmosis is referred to as a reverse osmosis membrane (RO membrane). Examples of the UF membranes can be represented as AFC99 manufactured by PCT Membranes.

Batch Process and Continuous Process

An exemplary diafiltration process in a "batch process" used in the present invention is an operating method including: storing a circulating liquid in a circulating system; adding a cleaning liquid from any device or pipe in the circulating system; extracting a permeate liquid out of the membrane module; and obtaining the residual liquid. The circulating system includes: a pump provided between a circulating liquid tank in which the circulating liquid is stored and a membrane separation apparatus; a circulating liquid tank; a pressure increase pump; a membrane separation apparatus; in some cases, a circulating pump in the membrane separation apparatus; a circulating liquid tank; and a pipe. Also, the batch process includes separation with a circulatory system established between a circulating liquid tank and multiple membrane separation apparatuses connected to the circulating liquid tank.

On the other hand, a diafiltration process in a "continuous process" herein includes: continuously supplying a prepared liquid to be processed to the membrane separation apparatus; adding a cleaning liquid; and extracting a residual liquid and a permeate liquid out of the apparatus.

Note that the batch process and the continuous process can be used in combination. For example, the entire process is conducted in the batch process but reception of the treating liquid and supply of the cleaning liquid are conducted in a continuous process. The residual liquid obtained by the process can be processed in a batch process and the product can be taken out in a continuous process.

Continuous Diafiltration, Continuous Multistage Diafiltration and Continuous Multistage Counter-Current Diafiltration The simplest continuous process according to the present invention includes: pressurizing the treating liquid and the cleaning liquid; supplying them to the membrane separation apparatus; obtaining the permeate liquid; and obtaining the residual liquid which has obtained the permeate liquid but has not permeated out of the membrane separation apparatus, Circulation through the circulating liquid tank, the pressure increase pump, the membrane separation apparatus and the circulating liquid tank can be established with or without the circulating liquid tank. The membrane separation apparatus can be implemented with or without internal circulation.

Also, multiple membrane separation apparatuses may be connected in series to form a multistage system. In this case, a process of supplying a fresh cleaning liquid to multiple stages can be implemented as a continuous multistage diafiltration process.

Multiple membrane separation apparatuses may be connected in series to form a multistage counter-current system. In this case, a process of supplying the cleaning liquid mainly to the last membrane separation apparatus and a pressurized permeate liquid given from the subsequent apparatus can be provided to other membrane separation apparatuses or can be conducted as a continuous multistage counter-current diafiltration process.

A combined process of the continuous process and the batch process can be conducted to include: continuously receiving an treating liquid in the circulating liquid tank; conducting processes using multiple membrane separation apparatuses while regulating concentration of the content, such as degree Brix, in the circulating liquid tank; temporarily storing the liquid processed in the apparatuses in an intermediate tank; stopping the supply of the treating liquid and completing the process of the treating liquid; then processing the liquid in the intermediate tank in the multiple membrane separation apparatuses; and continuously discharging the processed residual liquid out of the system.

In the processing of a liquid in membrane separation, cleaning of the membrane is typically important. In the batch process of the present invention, cleaning may be conducted after the liquid is processed. In the continuous process of the present invention, membrane cleaning is also required. Also, the washing can be conducted according to the operation status of the membrane or may be conducted regularly after a predetermined period of time. Thereby, an operation corresponding to the change of state in the membrane separation apparatus can be conducted by using the operating parameters, the separation status indices and the progress indices during the operating conditions of the membrane separation apparatus.

Internal Circulation, Circulating Liquid Tank, Circulating Liquid and Residual Liquid In the present invention, circulation formed by a circulating pump from an outlet to an inlet of the membrane module for securing a flow rate on the membrane surface in the membrane module is called "internal circulation", and the liquid used therefor is called an internal circulating liquid. Also, when a circulating liquid tank is used in the present invention, a circulating flow from a circulating liquid tank through a pressure increase pump, a membrane separation apparatus and the circulating liquid tank is called a "circulatory system", and the liquids circulating through the system is called a "circulating liquid".

The aforementioned internal circulating liquid and the circulating liquid may collectively be referred to as a circulating liquid. Also, the aforementioned circulating liquid may become a "residual liquid" after a certain process is completed.

Operating Parameters

In the present invention, operating parameters directly affect separation of target substances using a membrane. Parameters are set up as operating parameters in the membrane separation apparatus. The operating parameters are maintained, changed, regulated or controlled in a predetermined range, which may be a separation status index, or may be directly provided as an operating parameter based on a progress index.

Specific examples of the operating parameters may include: the flow rate of the permeate liquid from the membrane module of the membrane separation apparatus; operating pressure of the membrane separation apparatus, which may typically be an outlet of the membrane module or the pressure of the circulating liquid from the membrane separation apparatus; operating temperature of the circulating liquid (or the residual liquid); the hydrogen-ion density (pH); concentration of the circulating liquid used as a standard for the control by supplying a cleaning liquid; and the amount of the circulating liquid. The predetermined range of the operating parameters can be defined by the separation status index or the progress index in accordance with the membrane separation status, the operation status and the progress of the membrane separation operation.

In a example of the operation, a predetermined range of the flow rate of the permeate liquid is provided as an operating parameter, the flow rate of the permeate liquid which is the separated state index is controlled to the predetermined range by regulating the operating pressure while controlling the operation so that the operating temperature and the concentration of the circulating liquid remain constant. In this manner, the permeability may be controlled. A predetermined range of the flow rate of the permeate liquid is similarly provided as an operating parameter. A predetermined flow rate of the permeate liquid may be achieved by regulating a predetermined concentration value in the concentration of the circulating liquid control accompanied by the control of the amount of water supplied for diafiltration while controlling the operation so that the operating temperature and pressure remain constant. The circulating liquid temperature can be regulated by the amount of the supplied coolant. The concentration of the circulating liquid can be regulated by the amount of the supplied diafiltration liquid. The operating pressure can be regulated by the control valve provided at the circulating liquid or in the discharge system.

Note that a flow rate of the permeate liquid obtained from a membrane in the membrane separation apparatus using the same kind of membrane per unit time is usually used as the flow rate of the permeate liquid. The flow rate of the permeate liquid may be obtained from some or all of the membranes in the membrane separation apparatus, and may be expressed in terms of the permeation flux ($kg/m^2/hr$) or the flow rate of the permeate liquid. The predetermined range does not necessarily include the upper and lower limits and may alternatively be a target value.

Separation Status Index

A separation status index in the present invention is an index for quantizing the separation status of the membrane separation apparatus in operation, which can be used as the index for maintaining changing, regulating or controlling the predetermined ranges of operating parameters. Specific examples of the separation status index can be related indices including: measurement values and analytical values provided by a sensor or an analyzing device, including a refractive index, degree Brix, density, light transmission, electric conductivity and infrared spectrum and the like of the circulating liquid and/or the permeate liquid or the permeate liquid stored in a container; differential values obtained from the above measurement values or a progress index of the analytical values; that is, numerically processed values, such as differential values, a rate of change, average values and integral values obtained based on the elapsed time, the amount of permeate liquids and the amount of the cleaning liquids and the like; similar values for the circulating liquid; a ratio of the similar values of the permeate liquid and the circulating liquid; and a ratio of these values to the values actually obtained at the previous time.

In operation of the membrane separation apparatus, the separation status index may be used to select the operating parameters, provide a predetermined range in the separation status index, and regulate and control the operating parameters so that the corresponding separation status index obtained by measurement or calculation based on the measurement is controlled to the predetermined range. Predetermined range as operating parameter of flow rate of the permeate liquid and setup as separation status index.

The flow rate of the permeate liquid and the permeation flux can set a predetermined range as the separation status index and as the operating parameter. At first, if the predetermined range is provided with the flow rate of the permeate liquid being the operating parameter, the measurement value may be used both as the separation status index and the operating parameter. In this case, operation is conducted such that the value of the separation status index is controlled to the predetermined range by regulating, for example, the operating pressure while confirming the flow rate of the permeate liquid as the separation status index. In the next, if diafiltration is controlled with the measurement values and the analytical values obtained as the separation status indices being used for the control of the operating parameters other than the flow rate of the permeate liquid, the concentration of the circulating liquid, for example, may be regulated as an operating parameter so as to control the flow rate of the permeate liquid to the predetermined range.

That is, the flow rate of the permeate liquid and the permeation flux can be used as one or both of the operating parameter and the separation status index.

Progress Index

A progress index in the present invention is an index for quantizing a degree of progress of separation using a membrane or for determining the transition between operating stages or completion of an operation stage. The progress index may not only be a quantitative index to be summed up, such as time and liquid amount, but may also be an index representing separation results, such as concentration or a ratio of concentration of the residual liquid, the permeate liquid and the treating liquid, physical properties including viscosity, electric conductivity and pH, or the amount of the liquid to be supplied, such as the cleaning liquid. In some cases, the amount of the liquid to be processed which varies with progress of the separating operation, the measurement values, the analytical values and the calculated values of the liquid to be processed based on the measurement values and the analytical values, or the measurement values, the analytical values and the calculated values of the permeate liquid based on using the measurement values and the analytical values may also be used. A predetermined value of the separation status index corresponding to the value of the progress index may be set up. The predetermined value of the operating parameter corresponding to the value of the progress index can also be set up directly. The respective operating parameters can be maintained, changed, regulated, or controlled.

In a continuous process, the operation status of a membrane separation apparatus to be operated is recognized using the progress index to set up the operating parameter for each membrane separation apparatus.

Passage (or Described as Transmittance) and Rejection

Separating capability of target substances by a nanomembrane and a UF membrane in the membrane separation apparatus may be represented by passages (or described as transmittances) that are calculated as an apparent rejection Rapp of each substance (hereinafter, referred to as a "rejection") and a ratio of concentration Cp of one component of a target substance in the permeate liquid to the concentration Cb of the same component of a supplied liquid. Cp represents concentration of one component of target substance in permeate liquid (g/kg) and Cb represents concentration of the same component of supplied liquid to module (g/kg).

$$R_{app} = 1 - \frac{C_p}{C_b} \qquad \text{[Equation 1]}$$

Also, evaluation can be provided using concentration of the circulating liquid instead of concentration of the supplied liquid.

Control of Permeability

Transmittance for one component may be varied due to change in the flow rate of the permeate liquid and the permeation flux which are described above with reference to Tables 1, 2, 3 and FIG. 2. Tendency that a greater flow rate of the permeate liquid may reduce the transmittance, and vice versa, may be utilized. The flow rate of the permeate liquid or the permeation flux as the operating parameter, as shown in FIG. 2, is related to permeability of the components in a selected separation membrane or in the membrane separation apparatus. The transmittance may be varied due to change in the operating pressure or operating temperature of the membrane device. The flow rate of the permeate liquid may vary depending on various operations and permeability is also changed at the same time. Such a change may be made even on substances having mutually similar permeability, and the separativity may be controlled utilizing such a function.

In many cases, permeability of the batch process is controlled by regulating the operating pressure which provides a predetermined range of a preferred flow rate of the permeate liquid. The separativity is influenced by the state of the membrane, the temperature of the circulating liquid, the concentration of the circulating liquid, the pH and the amount of the circulating liquid. It is not necessary that the flow rate of the permeate liquid be constant. Variation in the flow rate of the permeate liquid has a significant influence on permeability. Permeability may be rapidly controlled by changing the flow rate of the permeate liquid. Permeability may preferably be controlled by recognizing the separation status indicated by the separation status index which reflects the composition of the permeate liquid, setting up, keeping, changing, regulating and controlling of the operating parameters, such as the flow rate of the permeate liquid and the operating pressure or predetermined ranges thereof. In some cases, membrane separation may be conducted suitably by setting up, keeping, changing, regulating and controlling the predetermined ranges for the operating parameters using the progress indices, such as the amount of permeate liquids, and elapsed time without using the separation status index.

Also, in operation, different conditions are provided all the time due to varying factors, such as introduction of heat from a pump or temperature of an introduced liquid, for temperature of the circulating liquid. On the other hand, the parameters to be controlled, can to include the flow rate or composition of the permeate liquid due to cooling or heating by a heat exchanger. Permeability can be regulated or controlled by the control of temperature or other operating parameters, such as pressure and concentration.

Furthermore, composition and the pH of the circulating liquid may influence the flow rate of the permeate liquid and the separativity. Concentration of the content in the circulating liquid measured in terms of, for example, degree Brix and electric conductivity may directly affect the flow rate of the permeate liquid. Furthermore, concentration can be controlled by changing a predetermined value of the amount of cleaning liquid and the circulating liquid to be supplied, or by regulating the return amount of the permeate liquid to the circulating liquid. The pH can be controlled by introducing acid or alkaline substances to adjust pH.

Permeability can be controlled by combining the sources of variation of permeability, and preferably by combining with the control by the operating pressure of the permeation flux. This can be conducted in both the continuous process and a combination of the continuous process and the batch process.

Measurement Value Regarding Composition, Concentration of Circulating Liquid, Concentration of Content Material In the present invention, measurement values regarding composition and concentration of the treating liquid, the circulating liquid at the time of starting up, the circulating liquid of the membrane separation apparatus, the permeate liquid and the like can be used as indices representing the state of the circulating liquid or the permeate liquid obtained by using sensors, such as a refractometer, a saccharimeter, a densimeter, a light transmission measuring device and an electric conductivity meter, may be used as an index indicating status of the circulating liquid and the permeate liquid. In particularly, in management of the circulating liquid for concentration of the circulating liquid and the amount of supplied cleaning liquid, it is important to appropriately manage an operation of the measurement value of composition and concentration of the circulating liquid, and the membrane separation apparatus. The composition and concentration of the circulating liquid directly affect permeability of the membrane. If the concentration is excessively high, progress of rapid fouling and shortening of operation durability may easily be caused. If concentration is low, the diafiltration effect may be reduced. Thus, the measurement values of for example, degree Brix, density, refractive index, electric conductivity and the like, are used for control of the circulating liquid. In a liquid containing multiple components, the measurement values of the components are complexly influenced by, for example, a composition ratio and temperature as well as total density of a substance or a substance group, however, it is not necessary, the case that the measurement values correspond with concentration of a substance or a substance group. It is therefore important to use such measurement values or values based thereon as indices for appropriate management of the amount of the circulating liquid and concentration. During measurement, it is desirable to conduct correcting temperature or managing temperature of the samples as needed. If the meaning concentration of the circulating liquid is used as concentration related to a density range suitable for membrane separation, in particularly, such concentration is referred to as the "sum total substance concentration."

Degree Brix and Degree Brix Ratio

"Degree Brix ratio" used in the present invention is represented by a formula [degree Brix of permeate liquid]/[degree Brix of circulating liquid]. The degree Brix ratio also can be used as the progress index and the separation status index. That is, with respect to the same circulating liquid, the degree Brix ratio becomes large in an operation with greater permeability and becomes small in an operation with smaller permeability. A predetermined range of the index can be provided to regulate and control the operating parameters. Also, the degree Brix ratio can also be used to switch the operation stages, or to detect an end point of the operation stage as a progress index of for membrane refinement.

Also, the degree Brix ratio and the degree Brix in the permeate liquid represent variation in permeability. In pressure-driven membrane separation, there is a relationship between the transmittances of the components as shown in FIG. 2 and it is considered to be common that variation in permeability occurs in connection with increase and decrease of the transmittance of the basic material or increase and decrease of other transmittances. The degree Brix or the degree Brix ratio of the permeate liquid with respect to the circulating liquids having the same concentration is represented as a transmittance, that is, as variation in concentration of each substance due to variation in separativity of each substance in membrane separation. Concentration of the permeate liquid of the circulating liquid after the operation from the circulating liquid of the same concentration at a starting point reflects both the currently achieved concentration through operation and current separating capability, and is able to be thus recognized as an index integrating both of them.

Degree Brix is measured in the same manner as a measurement principle of the refractive index, and can be adapted for glycerins and glycols other than saccharide. In addition to the degree Brix, electric conductivity and density of total organic carbon (TOC) and a liquid density standard can be used as indices in the same manner as in the degree Brix and are also respectively important as the separation status indices.

Precise Fractionation

"Precise fractionation" in the present invention is defined as "mutually separating substances having closely similar permeability." In particular, precise fractionation is defined as "in separation using a membrane which promotes permeation of 'target substances which are permeable and are preferably permeated' and blocks 'target substances which are hardly permeable and are not preferably permeated,' the 'target substances which is preferably permeated' is recovered at a high recovery rate into the final permeate liquid, separation is conducted at high concentration with a reduced remaining rate in the final residual liquid, and the 'target substances which is not preferably permeated' is separated into the final permeate liquid at a high recovery rate and high concentration with reduced remaining rate in the final residual liquid."

Index for Controlling State of Flow

An index provided by integrating variation in density or viscosity, such as pressure difference of the inlet and outlet of the membrane module, may be used to control concentration of the circulating liquid. Concentration of the circulating liquid can be controlled by, for example, adding a cleaning liquid so that the pressure loss becomes a certain value or less. For example, it is possible to operate with the concentration being in a range which does not affect membrane separation by making the pressure loss constant.

Method of Operating Membrane Separation Apparatus of the Present Invention

Specific methods of operating in the present invention will be illustrated below.

FIG. 1: Example of Batch Operation

Referring now to FIG. 1, an exemplary batch operation will be described.

FIG. 1 shows a flowsheet illustrating the entire apparatus adapted for batch diafiltration having a single membrane separation apparatus according to the present invention. This apparatus does not use no internal circulation. A circulating liquid tank 1 is a container of any shape made of, for example, metal or synthetic resin. The circulating liquid tank 1 may have a bottom through which the total content of the liquid in the tank may be discharged. It is preferable that weight, liquid level and the like can be monitored continuously so that the amount of liquid remaining inside can be detected. It is preferable to clean the tank 1. The circulating liquid tank 1 can include a pH meter 8, a thermometer, a function to measure concentration of the circulating liquid 26, a mechanism for maintaining temperature of the circulating liquid 29, a mechanism for regulating the return amount of the permeate liquid to the circulating liquid 30, a mechanism for supplying treating liquid 21, a mechanism for extracting the circulating liquid 22, a mechanism for supplying the cleaning liquid 23 and the like. These components may be connected or attached to a circulating liquid outlet pipe/hose 10 or an inlet pipe for the pressure increase pump 3.

The circulating liquid tank 1 can include a function for mixing the received liquids which mixes the received liquids and introduces what in the tank 1, a stirring mechanism, a baffle plate, an oscillation mechanism, a showering mechanism for the purpose of preventing occurrence of unnecessary concentration distribution within the tank, deposition of solid content and sticking of substances to wall surfaces, an external circulation pump and a measuring mechanism for management of concentration of the circulating liquid, such as a saccharimeter and a densimeter. In order to effectively utilize concentration difference between a liquid which has stayed in the circulating liquid tank 1 for a long time and a liquid just introduced therein, the circulating liquid tank 1 can have a function to divide the inside into compartments. For example, the circulating liquid tank 1 may have a function to re-connect the compartments to cause the liquid in the tank to move and a function to switch a tank which sequentially receives a liquid and a tank from which the liquid is extracted so that multiple compartments may be used as an integrated circulating liquid tank 1.

Also, the circulating liquid tank 1 can to have a function to prevent leakage of gas or odor relating to the gas phase, such as a gas seal function if needed. A scale 2 for the circulating liquid tank is used to measure the amount of the liquid in the circulating liquid tank in terms of weight. The circulating liquid also exists in the membrane separation apparatus and in the pipe as well as the circulating liquid tank and the total amount of the circulating liquids, such as the total weight, cannot always be recognized. It suffices, however, that the amount of the liquid in the circulating liquid tank may be managed from the viewpoint of operation management.

The inlet pipe for the pressure increase pump 3 is connected with the circulating liquid tank and with the pressure increase pump 4. A container 11 for circulating warm water for cleaning the membrane, a cleaning liquid pump 14, a container 12 for extracting the circulating liquid and a strainer and a filter for pump protection can be connected to the pump inlet pipe 3.

Also, as described above, the circulating liquid tank 1 can to have a stirring function to prevent the occurrence of unnecessary concentration distribution within the tank, a function to prevent deposition of solid content, a vibrating function, a showering function and a function to prevent substances sticking to the tank. In order to improve the separation effect using a membrane, the circulating liquid tank 1 can be divided into multiple compartments. The compartments can be used in connection with each other or multiple compartments can be alternately used to provide staged progress of change in concentration of the circulating liquid.

The membrane separation apparatus includes a pressure increase pump 4, a pressure meter 7, a heat exchanger 5, a membrane module A 6A, a membrane module B 6B, a membrane module C 6C, a pressure control valve 9 and a connection pipe. The circulating liquid at an outlet of the pressure control valve 9 may be introduced into the circulating liquid tank 1 via, for example, the circulating liquid outlet pipe/hose 10. AFC80, which is a RO membrane, can be loaded in the membrane module A 6A and AFC30 can be loaded in the membrane module B 6B and in the membrane module C 6C. Here, AFC30 is used for the purpose of separating and refining a material of interest. AFC80 is used to regulate concentration. In normal operation, all the permeate liquids are returned to the circulating liquid tank 1 except for during regulation of concentration of the circulating liquid and cleaning of the membranes.

Operating pressure of the membrane module is recognized from the pressure meter 7. The pressure meter can be provided at any process location from an immediate downstream of the pressure increase pump to the pressure control valve. The pressure meter 7 may, however, desirably be located at a measuring point upstream or downstream of the membrane module where the pressure is most reflected. The pressure meter 7 may also be provided at a position where the representative membrane module is detected or at a position where pressure of the entire membrane module group is detected in a configuration with multiple membrane modules arranged in parallel. Similarly, the pressure meter can be provided downstream of the membrane module and also, a differential pressure meter can be provided in addition to the pressure meter to measure the differential pressure between the upstream side and the downstream side of the membrane module.

Pressure of the membrane module is usually regulated by the pressure control valve. Other methods, for example, however, may also be employed including a pressure regulating mechanism which uses a return line from the outlet of the pressure increase pump to the circulating liquid tank, or may also control of the rotational speed of the pressure increase pump using an inverter.

The heat exchanger 5 may be provided at a downstream of the pressure control valve or at the circulating liquid tank other than the outlet of the pressure increase pump 4. The heat exchanger 5 may preferably have heating and cooling functions. It suffices, however, that temperature of the circulating liquid may be controlled to a desired range if the heat exchanger 5 only has a cooling function or a heating function. The heat exchanger can be also used for the purpose of sterilization and preservation during membrane cleaning.

The cleaning liquid storage tank 13 is connected to the cleaning liquid pump 14 at a liquid supply side thereof via a hose or a pipe. The cleaning liquid storage tank 13 is also connected to the circulating liquid tank 1 and/or the circulating liquid pipe/hose 10 and the inlet pipe for the pressure increase pump 3 so that the cleaning liquid can be directly supplied. Supply of the cleaning liquid via the cleaning liquid pump is managed by keeping and controlling the predetermined concentration of the circulating liquid using a regulating valve or by supplying the circulating liquid to the circulating liquid tank at a predetermined flow rate. A cleaning process using detergent or a solvent may be applied to systems, such as the membrane separation apparatus 20, the circulating liquid tank 1 and other pipes using a liquid in the cleaning liquid storage tank or a separately prepared liquid. With this cleaning liquid, membrane cleaning is conducted upon necessity. The membrane cleaning liquid can be subject to pretreatment such as heating, cooling, concentration, refinement and separation through, for example, membrane separation, pH adjustment, chemical addition and the like.

The permeate liquid of the membrane module A, the membrane module B and the membrane module C is stored in a permeate liquid container and is used to, for example, measure the amount of the permeate liquid, to provide a permeate liquid sample and the like. The permeate liquid container may be made of metal, plastic or other materials and may be of any shape. The permeate liquid can be disposed in a selected process, for example, can be discharged out of the system directly.

If needed, the permeate liquid can be introduced into, for example, plastic containers via the pipe/hose for the permeate liquid 16 from upper nozzles of the membrane module B and the membrane module C.

The flow rate of the permeate liquid can be preferably measured constantly by a dedicated flow meter. The flow rate, however, can be calculated based on measurement values and elapsed time according to the variation speed of weight or variation speed of the liquid level of the permeate liquid tank.

It is considered that a relationship exists between the transmittance of the permeate liquid of the NF membrane or the RO membrane and the amount of the flow rate of the permeate liquid or the permeation flux, which is represented by the equation below. The greater the permeation flux J becomes, the smaller the transmittance becomes.

$$1/\text{Transmittance} = 1 + Jx(1/B)$$

wherein Jv represents a permeation flux (m/sec in the reference) and Bav represents a solute permeation coefficient (m/sec in the reference).

If two-staged membrane modules arranged in series is used, the permeate liquid may be obtained separately from the modules into different permeate liquid containers 15. It is preferable that the permeate liquids are obtained while a mechanism for measuring flow rate of the permeate liquid 25 obtaining measurement values of the flow rate which may significantly affect the membrane separation.

During membrane cleaning and pre-preparation, the permeate liquid may be introduced in the circulating liquid tank, the container 11 for circulating warm water for cleaning the membrane or the container 12 for extracting the circulating liquid. Hereinafter, the pipe/hose for permeate liquid 16, the drain hose 17, the permeate liquid container 15, the mechanism for 25 measuring flow rate of the permeate liquid, the mechanism 28 for measuring concentration of permeate liquid, a function to extract the permeate liquid out of the system and part or all of the permeate liquid may collectively be referred to as a mechanism 24 for extracting the permeate liquid to be returned to the circulating tank.

The circulatory system during normal operation of the membrane separation apparatus includes the circulating liquid tank 1, the inlet pipe for the pressure increase pump 3, the pressure increase pump 4, the heat exchanger 5, the membrane module B 6B, the membrane module C 6C and the pressure control valve 9. The circulating liquid tank can be changed as the container 11 for warm water circulation when the membrane cleaning liquid is circulating.

It is preferable that the operation, stopping, and security of the membrane separation apparatus can be maintained by a control mechanism, such as a control panel 18. The operation system and the control method can be suitably selected from, for example, automatic control for the entire operation, semi-automatic control, such as manual operation, for switching, manual control for the operation and the like.

The amount of the circulating liquid or the amount of circulation tank internal liquid is preferably managed by keeping concentration of the circulating liquid appropriately. Alternatively, concentration of the circulating liquid may be controlled by a function to measure concentration of the circulating liquid 26 and a mechanism for maintaining concentration of the circulating liquid 27 which controls the amount of the supplied cleaning liquid. And also, the predetermined weight of the circulating liquid tank can be determined or changed by a mechanism for regulating weight of the circulating liquid tank in the circulation tank while measuring concentration of the circulating liquid suitably.

The weight of the circulating liquid tank can be determined and changed by supplying the cleaning liquid at the weight corresponding to the weight of the obtained permeate liquid. For example, the predetermined value of the weight of the circulating liquid tank shown in the following equation can be controlled by calculating predetermined values for the amount of the permeate liquid obtained at the stage and the amount of the circulating liquid tank which is ever-changing from the input constant, and the cleaning liquid can be added to the circulating liquid tank so that the weight of the circulating liquid tank becomes the predetermined value.

[predetermined value of circulating liquid weight]= [predetermined value of the amount of circulating liquid at start point of a stage]−[Rate of change]×[obtained amount of permeate liquid].

Note that the rate of change is determined for concentration of each component of the circulating liquid, transmittance of each component and operation history and is determined for each stage of the diafiltration step.

Also, as a similar method, the amount of the circulating liquid and concentration of the circulating liquid may be controlled substantially by determining an ever-changing amount of the circulating liquid (WL) based on the amount of the cleaning liquid to be used (WWS), the initial weight of the circulating liquid tank (WLS), the final weight of the circulating liquid tank (WLE), the ever-changing amount of the permeate liquid (WP). Exemplary equation is given below.

$$\text{Circulating liquid } WL = WS + (WE - WS) \times WP/(WS - WE + WWS)$$

With the predetermined values corresponding to the above equation, the total content of a prepared cleaning liquid may be used and the weight of the initial weight of the circulating liquid can be changed on average to the amount of the circulating liquid after the washing investigation.

Functions to control, monitor and record, such as a in the form of a control panel, is preferably provided in order to control the measurement value of the circulating liquid temperature in the downstream of the pressure control valve 9 to the predetermined value. Such functions may include a mechanism for regulating circulating liquid temperature 29 which controls supply of cold water from a cold water unit 19, a mechanism for displaying the total weight of the permeate liquid, a function to display the flow rate of the permeate liquid based on the change of the weight of the permeate liquid over time and the time duration, and a function to display degree Brix in the circulating liquid for displaying degree Brix in the downstream of the pressure control valve 9.

Various commercially available measuring devices and analyzing devices may be used for measurement and analysis of the circulating liquid and the permeate liquid. Devices for continuous measurement may preferably be used. Portable devices may also be used for measurement and analysis by taking samples.

Preparation of Operation

Regarding operation of the apparatus for batch diafiltration, the inside of the apparatus and the separation membrane will be cleaned using detergent or a solvent. If needed, pretreatment conditions or operating conditions can be suitably selected according to the separating conditions using the separation membrane. For example, the pretreatment may include operating the separation membrane at normal temperature after operating at temporality high temperature, alternatively, operating the separation membrane under normal operating conditions after the membrane is adjusted while being maintained in a state with a temporarily high pH.

Before the operation is started, the conditions suited for target fractionation are roughly determined. The operating conditions have a direct influence on the operating performance. Concentration of the circulating liquid, the temperature and the pH of the circulating liquid may have upper and lower limits. For the operation of the membrane separation apparatus, upper and lower limits may be given regarding, for example, temperature, pressure, pH, pressure loss, viscosity and the like. Accordingly, appropriate operating conditions may be determined through tests under conditions to be appeared more suitable. Types of membranes may also be selected in the same manner.

Also, not in general, in many cases, the operating conditions and a degree of influence may be studied based on empirical rules, although not commonly accepted, that "higher pH tends to provide permeability of a separation membrane," or "higher operating temperature tends to provide a greater flow rate of the permeate liquid" for various substances.

Then, the flow rate of the permeate liquid is selected as the most sensitive operating parameter regarding operation in which the flow rate of the permeate liquid may be controlled. Data on the separation test is collected in correspondence with other conditions to be operated, such as pH, temperature and the like, so as to select the operating conditions suited for separation, including the permeation flux and the flow rate of the permeate liquid corresponding to suitable conditions.

Operation

Although detailed examples of the operation will be described in Examples, operating pressure, module positions, extraction of the circulating liquid, diafiltration and maintenance and changing of permeability in operation will be described below.

Measurement of Amount and Concentration of Permeate Liquid, Module Position, Operating Pressure and Flow Rate of the Permeate Liquid Measurement of the amount of the permeate liquid from the membrane device or the membrane module when the membrane separation apparatus is in operation can be conducted at various positions. Samples of the permeate liquid can be obtained at various positions. Selection of the positions may have influence on the operation and can be conducted in the following manner. The mechanism 25 for measuring the flow rate of the permeate liquid and the mechanism 28 for measuring concentration of the permeate liquid may be set for the purpose of the entire permeate liquid of the entire membrane separation apparatus or average values, or may represent a part for the membrane modules.

If the membrane modules are connected in series, the permeate liquid may be used at either the upstream or downstream side. Thereby, the membrane module of the downstream side, however, with lower pressure at the side of the circulating liquid usually has smaller permeation flux and higher concentration of the permeate liquid, which can provide concentration measurement sensitively reflecting the state of the circulating liquid. The module of the upstream side has higher pressure and larger permeation flux. Accordingly, the module of the upstream side reflects average composition of the permeate liquid which provides average concentration of the permeate liquid.

If the pressure is lowered to reduce the flow rate of the permeate liquid so as to increase concentration of the substance to be permeated, the flow rate of the permeate liquid decreases due to influence corresponding to the osmotic pressure. No permeate liquid may therefore be obtained from the module provided in the downstream side. In consideration of these facts, positions of the mechanism 25 for measuring the flow rate of the permeate liquid and the mechanism 28 for measuring concentration of the permeate liquid, and predetermined ranges of the operating parameters should be selected by appropriately.

The circulating liquid can be extracted as the final residual liquid when it is determined that the batch separation is completed. If it is more advantageous to increase concentration when the batch separation is determined to be completed, the operating pressure is increased temporarily to increase concentration of the circulating liquid and then the circulating liquid and the permeate liquid can be extracted. If the measurement value and the analytical value of the permeate liquid are used for control or determination, the liquid in the module and in the pipe may be discharged as a drain for measurement and then the permeate liquid may be obtained for measurement and analysis in order to eliminate influence of the liquid resulting from the permeate liquid accumulated in the module. This may be effective in terms of response of control or various timing selection, and may also be effective in switching of the stages or determining timing of completion.

If multiple modules are provided, the drain does not reflect concentration of the entire permeate liquid. It is therefore preferable to consider a relationship between the flow rate of the permeate liquid and the measurement value or the analytical value for determination.

The circulating liquid may be extracted by using a mechanism 22 for extracting the circulating liquid, by being discharged out of the system from the circulating liquid tank using a pressure increase pump and/or an internal circulation pump or by transferring to a separately prepared container or a storage tank via the circulating liquid outlet pipe/hose 10.

Extraction of Circulating Liquid

The residual liquid can be extracted directly from, for example, the circulating liquid tank using a pump upon completion of the diafiltration process. Also, the circulating liquid remaining in the membrane separation apparatus or the circulation pipe can be discharged out of the system using the cleaning liquid or warm water. The remaining liquid can be conducted by a method combined with taking spraying of the cleaning liquid into the internal circulation tank.

Control of Permeability

It is possible to provide separating performance according to separation status of the circulating liquid or the permeate liquid as the process of diafiltration proceeds if the predetermined range of the operating parameter is fixed or may be changed gradually or in a stepped manner. Other operating parameters may preferably be changed as needed so as to change the flow rate of the permeate liquid in accordance with the separated state index or the progress result index.

Also, separating performance according to separation status of the circulating liquid or the permeate liquid may be provided as the process of diafiltration proceeds if the predetermined range of the operating parameter is fixed or may be changed gradually or in a stepped manner.

Furthermore, the diafiltration process can be divided into multiple stages and predetermined ranges of operating parameters may be provided for each stage. That is, by changing the predetermined ranges of the flow rate of the permeate liquid, the operating pressure, the operating temperature and the pH through chemical addition, the predetermined ranges of the operating parameters for each stage are controlled to achieve separation status desired for membrane separation at each stage while managing completion and the starting of each stage. In this manner, regarding desired separation for the entire diafiltration process, repeatedly conducted diafiltration processes may provide separation results suitable for separation purposes.

Description on Variation in Degree Brix of Mixture Through with Changed Flow Rate of the Permeate Liquid A liquid containing 10% of a substance A and 10% of a substance B having transmittances of 0.1 and 0.0, respectively, in an initial operating condition is prepared. The percentage is equivalent to the degree Brix hereinafter. The liquid is subject to an operation while reducing the concentration of the substance A by a diafiltration process and maintaining a total degree Brix at 20%. The concentration of the substance B is made to increase and approach 20%. Here, the degree Brix and the total amount are gradually reduced so that concentration of the substance A is made to decrease and approach 0%.

Supposedly, in an operation in which the original flow rate of the permeate liquid is maintained, the degree Brix is measured to be 0.15% (1.5%×0.1) when concentration of the substance A is 1.5% and the transmittance is 0.1. If the limit of measurement of a saccharimeter is 0.2%, this state cannot be detected. If the apparatus is operated, however, with the reduced flow rate of the permeate liquid and a transmittance of 0.2, the degree Brix of the permeate liquid becomes 0.3% (1.5%×0.2), which may be detected by the saccharimeter. Such a phenomenon based on the description above may be applied to decisions during operation, such as detection or confirmation of concentration of the permeate liquid or the circulating liquid at appropriate times including, as well as, at start, at end and at of switching.

Also, in separation of a multicomponent mixture system containing a large amount of substance A which easily permeates a membrane, a substance B which hardly permeates and thus is not intended to permeate a membrane and a substance C having middle permeability with respect to those of the substances A and B. If the substance C is to be removed while maintaining the substances A and B, the operation is started with low permeability mainly to cause the substance A to permeate, and then causes the substance B to permeate, thereby, permeation of the substances A, B and keeping of C can be achieved.

The separating performance in diafiltration is improved with a smaller volume of the circulating liquid and a higher concentration of target substances. Thereby, for example, diafiltration may proceed efficiently when concentration of the circulating liquid is appropriately maintained by using a saccharimeter at the stage of diafiltration. It is not always preferable, however, to keep the concentration high. For security in operation or protection of a surface, the predetermined range may preferably be loosely defined.

Also, a large amount of permeable substance is contained in a liquid immediately after introduction. It is also possible to manage concentration of the circulating liquid or the internal circulating liquid only in the stage where composition of the circulating liquid changes greatly and, in other stages, to manage parameters other than concentration, e.g., the amount of liquid.

Figure 3:
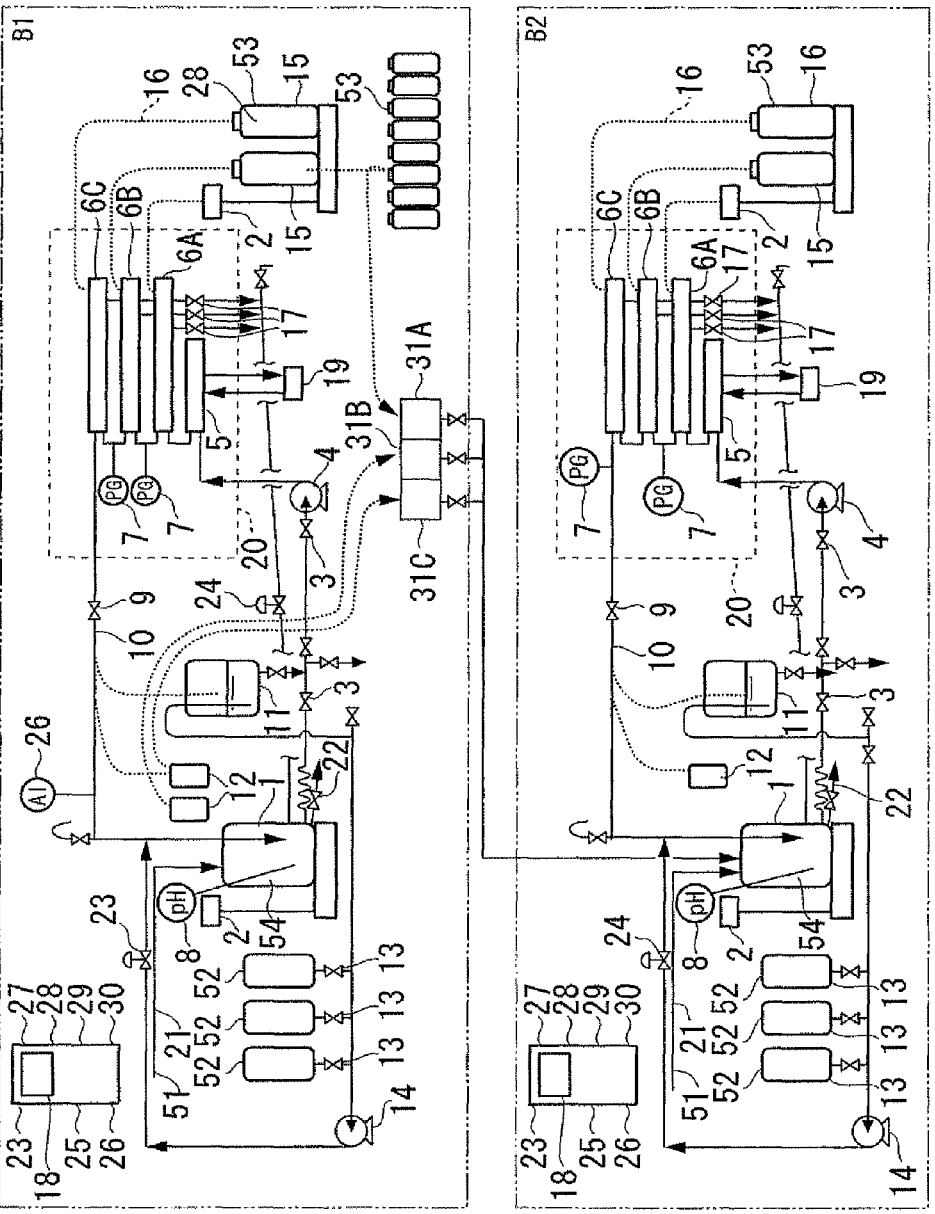
FIG. 3 is an exemplary flowsheet of a continuous diafiltration process.

Exemplary Operation with a Processing Liquid Used Over Multiple Batch Operations (FIG. 3)

FIG. 3 shows a flowsheet illustrating the entire apparatus for conducting diafiltration over multiple batch operations according to the present invention. Description will be given below with reference to the flowsheet.

Since the entire configuration in FIG. 3 is almost the same as that of the batch operation in FIG. 1, similar components are denoted by similar reference numerals. The difference therebetween will be described below. A section enclosed by a two-dot chain line labeled with B1 in FIG. 3 corresponds to a first batch operation and a section enclosed by a two-dot chain line labeled with B-2 corresponds to a second batch operation. The first and second batch operations are conducted in the same apparatus in this order.

In an operation with multiple batch processes, a residual permeate liquid in the previous batch operation, that is, a diluted liquid produced when the permeate liquid used in the previous batch operation or a finally remaining circulating liquid are removed out of the system, is used as a mixture liquid with a cleaning liquid or an treating liquid, or a reprocessed liquid. The apparatus requires containers for storing those liquids. These containers are collectively referred to as a previous batch liquid storage tank 31, in which a section for storing a previous batch "permeate liquid" is labeled with 31A, a section for storing a "dilute liquid produced during extraction of the final circulating liquid" is labeled with 31B and a section for storing a "reprocessing liquid" is labeled with 31C.

FIG. 3 consists of two sections. The upper section is a batch device in which processes obtained from an operation flow in the previous batch process. The liquid is supplied through 31A, 31B and 31C described above to a section where the liquid is typically used in the batch operation flow, which will be conducted later.

The previous batch of the "permeate liquid," "dilute liquid by extraction of the final circulating liquid" and "reprocessing liquid", which will be described later, may be used in the subsequent batch, thereby, with to improved totally recovery rate of the target substance and decreased loss.

Exemplary use of the liquids from the previous batch in the subsequent batch will be described.

The "dilute liquid by extraction of the final circulating liquid" is a part of the residual liquid recovered as a dilute liquid by discharging a liquid from the circulation liquid tank, the membrane separation apparatus or related pipes using a cleaning liquid, such as warm water. The residual liquid has already undergone the separating operation and contains substances intended to permeate in membrane separation whose concentration level is lower than required. Then, this liquid may be used as a cleaning liquid as it is, or may be used in a later-conducted batch process together with dilute liquids produced in several batch processes. Although it is also possible to only condense these liquids to be removed as an fractionated residual liquid out of the system, if the liquid is used as a part of a material or the cleaning liquid, unnecessary concentration and preservation of the cleaning liquid can be avoided.

The "dilute liquid by extraction of the final circulating liquid" can be suitably used as a leading portion of the cleaning liquid at the final process stage. The dilute liquid may preferably be introduced through a pipe of the cleaning liquid during managing concentration of the circulating liquid. Such a method may include directly introducing the dilute liquid in the circulating liquid tank 1, using the concentrated dilute liquid as the cleaning liquid or introducing in the circulating liquid tank 1 after the concentration.

The "reprocessing liquid of the previous batch process" may be reprocessed if it is determined in an analysis after the separation in the previous batch process that separation is not completed and that impurities need to be refined again.

The "reprocessing liquid of previous batch" is not necessarily introduced simultaneously with the treating liquid of the subsequent batch, and can be used as a leading portion of the cleaning liquid at the final process stage. The reprocessing liquid can be preferably introduced into the circulating liquid in the same manner as in the "dilute liquid by extraction of the final circulating liquid."

The "permeate liquid of the previous batch process" may be used in the following manner. A single batch process is divided into multiple stages. A fresh cleaning liquid is used as a cleaning liquid in the final stage. In other stages, the permeate liquid succeeded from the previous batch process, or the residual liquid and the permeate liquid which is condensed by using a membrane used in a normal batch operation or the RO membrane, NF membrane and UF membrane of a separately-provided membrane separation apparatus can be used as a cleaning liquid instead of a fresh cleaning liquid. Here, a part of the target substance can be extracted out of the system at the concentration step into the permeate liquid.

The "permeate liquid of the previous batch process" can be used only at, for example, the beginning of the diafiltration process for each stage in order to provide a cleaning effect before starting the diafiltration process. The "permeate liquid of the previous batch process" can be conducted preferably into the circulating liquid in the same manner as in the "dilute liquid by extraction of the final circulating liquid."

Exemplary Continuous Multistage Diafiltration (Relationship in FIG. 4)

FIG. 4 shows a flowsheet illustrating the entire apparatus for conducting continuous multistage diafiltration according to the present invention. A description will be given below with reference to the flowsheet.

The membrane separation apparatus 20 includes, as principle components, a heat exchanger 5, a membrane module 6, a pressure meter 7 and a pressure control valve 9 as in the configuration shown in FIG. 1. Such a configuration may be provided with or without an internal circulation pump 32. However, if the internal circulation pump is provided, it is attached to each membrane separation apparatus 20. If the internal circulation pump is not provided, the circulation may be established with the circulating liquid tank 1 or the pressure increase pump. FIG. 4 illustrates a configuration with the internal circulation pump 32.

The treating liquid 51 is introduced into the circulatory system by a pressure increase pump. The circulatory system includes a cleaning liquid 52, the internal circulation pump 32 of the membrane separation apparatus 20A, the membrane module 6 and the heat exchanger 5. Here, the diafiltration process is divided into three stages and the membrane separation apparatus 20A, 20B and 20C are used.

The treating liquid is subject to diafiltration using the cleaning liquid 52 in the membrane separation apparatus 20A. The permeate liquid is extracted and the residual liquid is sent to the membrane device 20B via the pressure control valve 9. The treating liquid is also subject to diafiltration using the cleaning liquid 52 in the membrane separation apparatuses 20B and 20C. Finally, the residual liquid is obtained.

The membrane separation apparatus 20, the internal circulation pump 32, the membrane module 6 and the heat exchanger 5 altogether form a circulatory system in each of the stages.

The operating pressure of each stage is controlled by controlling the amount of the circulating liquid to be discharged to the subsequent stage or out of the system via the pressure control valve. The flow rate of the permeate liquid from each membrane separation apparatus is measured. The operating parameters, such as the flow rate of the permeate liquid, operating pressure, operating temperature and operation concentration are determined so that the separation status index is within a predetermined range for separativity control. The permeate liquid may be transferred out of the system, transferred to a previous stage as the cleaning liquid or may be returned to the membrane separation apparatus of the same stage. Part of the permeate liquid may preferably be used to control the return amount to the membrane separation apparatus at the same stage to a constant liquid level in the permeate liquid container.

Operation of the continuous multistage diafiltration in the present invention is conducted while controlling permeability of the membrane separation of the operation status as in FIG. 1 and FIG. 3. In particular, the temperature of the circulating liquid is regulated using a heat exchanger of each membrane separation apparatus. The operating pressure is controlled so that the flow rate of the permeate liquid is in a suitable range. In this manner, concentration of the circulating liquid and concentration of the permeate liquid may be monitored or controlled. This applies to both the batch operation and the continuous operation. Unlike the batch operation, the continuous operation needs to detect ever-changing status of the circulating liquid and the permeate liquid in each of the stages in detail.

In the multistage continual process shown in FIG. 4, the supplied treating liquid is subject to a batch or continuous process, and then supply of the treating liquid to the liquid stored in the circulating liquid tank 1A is stopped to perform diafiltration. Diafiltration may alternatively be performed with the treating liquid being continuously supplied. Three membrane separation apparatus 20A, 20B and 20C are provided here. Operation proceeds from the first stage to the third stage in each of the membrane separation apparatus.

In particular, the concentration-regulated treating liquid 51 is first supplied to the circulating liquid tank 1A. Diafiltration proceeds in the membrane separation apparatuses 20A (20B, 20C) equipped with the membrane module using the pressure increase pump 4 with the treating liquid being continuously supplied. The residual liquid is transferred to the subsequent membrane separation apparatus 20B.

During this process, the cleaning liquid is introduced between the pressure increase pump 4 and the membrane separation apparatus 20A (20B, 20C) or in the circulatory system of the membrane device. The permeate liquid is then obtained from the membrane separation apparatus 20A (20B, 20C) and is stored in the permeate liquids container 15A (15B, 15C). The membrane separation apparatus 20A (20B, 20C) operates using a similar liquid to be processed (i.e., the treating liquid 51 and an in-process treating liquid 51) and obtains the cleaning liquid 52, the permeate liquid 53 and the residual liquid 54. The circulation or a cross flow in each membrane separation apparatus may be provided with or without using the internal circulation pump 32. The foregoing description has been given to the configuration with internal circulation.

Regarding a method of controlling membrane permeability in the continuous multistage diafiltration process, the flow rate of the permeate liquid in each membrane separation apparatus can be regulated by the flow rate of the permeate liquid obtained from the membrane separation apparatus or the flow rate of the permeate liquid obtained from a selected module. Operating pressure of the membrane separation apparatus, operating temperature, concentration of the circulating liquid and hydrogen ion concentration (pH) can be controlled or regulated with respect to the circulating liquid as in the batch operation.

Concentration of the circulating liquid or the internal circulating liquid is controlled by controlling the amount of supplied cleaning liquid via the cleaning liquid regulating valve 33 so that concentration, such as in terms of degree Brix of the circulating liquid, is within a predetermined range. The separation status index, such as the degree Brix of the permeate liquid, and the flow rate of the permeate liquid are measured for each membrane separation apparatus. The flow rate of the permeate liquid is suitably determined using the separation status index, such as the degree Brix.

Pressure of the circulating liquid is regulated by the pressure control valve 9 provided in a pipe for discharging the circulating liquid to the subsequent membrane separation apparatus or out of the system. It is also possible to perform diafiltration by establishing a circulatory system in which the circulating liquid runs through the circulating liquid tank 1, the membrane separation apparatuses 20A, 20B and 20C and returns to the membrane separation apparatus 20A with reference to the process flowchart of FIG. 4.

Also, diafiltration in accordance with the process flowchart of FIG. 4 may be conducted with the treating liquid being continuously supplied. The processed liquid may be stored in the circulation liquid tank 1B. Supply of the treating liquid is then stopped and the liquid in the circulating liquid tank 1B is subject to final diafiltration. The process is repeated from 1A to 1B and from 1B to 1A so that the three-stage apparatus can be repeatedly used several times for the treating liquid in one batch process.

Furthermore, the permeate liquid pump 34 shown in FIG. 4 may help return the permeate liquid to the circulatory system in which the permeate liquid is generated. In particular, regarding the flow rate of the permeate liquid obtained from the process of maintaining suitable separativity in the membrane separation apparatus, an extra amount of the flow of the permeate liquid transferred from the circulatory system of the membrane device out of the system is returned to the circulatory system of the membrane separation apparatus. In this manner, a normal and steady operation status may be provided. On the other hand, if it is necessary to reduce the amount of the permeate liquid from a target membrane separation apparatus, a liquid to be processed can be condensed in advance to reduce the amount of the permeate liquid processed in the membrane separation apparatus.

In this case, a sufficient amount of permeate liquids can be provided with increased surface area to be used in the membrane separation apparatus so as to reduce the flow rate per unit area.

The cleaning liquid can be replaced by the permeate liquid obtained in each stage. In this case, the permeate liquid is also preferably circulated to the stage where the permeate liquid is produced.

The circulation tank 1 shown in FIGS. 1, 3 and 4 can be used effectively when divided into several compartments. Alternatively, several circulation tanks 1 may be provided. Especially in the batch process, since the liquid to be processed has an ever-varying composition, that is, since the divided circulation tank 1 may have a circulating liquid which has been subject to diafiltration for a long time in the upstream side and have a circulating liquid which has not been subject to diafiltration in the downstream side by causing the liquid to be supplied for a long time in the upstream of the divided circulation tank 1 and to move toward the downstream as diafiltration proceeds, efficient diafiltration can be provided as compared to a configuration using an uniformly-mixed circulating liquid.

Also, a plurality of circulation tanks 1 may be provided for alternate use to provide similarly efficient separation. That is, if the circulation tanks 1A and 1B are provided, a liquid to be processed is supplied to the membrane separation apparatus from the circulation tank 1A and the residual liquid is continuously supplied from the membrane separation apparatus to the circulation tank 1B. After the circulation tank 1A is emptied, the operation from the circulation tank 1A to 1B is switched to the operation from the circulation tank 1B to 1A.

Example 1

In this example, a polyglycerin mixture, containing glycerin, diglycerin, triglycerin, tetraglycerin, and higher polymerization degree polyglycerins than them which is usually available as "decaglycerin" (in Japan) is used as an treating liquid, and refined using a membrane. Degree Brix of the permeate liquid from the membrane separation apparatus using a nanomembrane is recorded sequentially. When degree Brix reaches the predetermined value, the operating pressure is reduced, thereby reducing the amount of glycerin and diglycerin to one tenth of the initial state.

| Treating liquid | |
| --- | --- |
| Materials composition, Moisture | 28.7 wt % |
| polyglycerin total density | Balance |
| Average degree of polymerization | Decamer |

Method of Analysis

The obtained product is dehydrated in a concentrating device to provide a concentrated sample. An internal standard liquid is prepared by adding a certain amount of pyridine to tetradecane. The internal standard liquid, hexamethyldisilazane, chloro methylsilane, and chloro trimethylsilane are added to the concentrated sample, which is heated, trimethylsilylated and then analyzed by gas chromatography. Data with regard to composition shown in Table 5 is the index obtained by an area ratio through gas chromatography with respect to the internal standard substance added to the dehydrated, concentrated sample.

Apparatus

The membrane separation apparatus will be described in detail below.

A membrane separation apparatus BRO/BUF manufactured by PCI Membranes loaded with a membrane AFC30 in two 1.2 m B1 membrane modules is used. A membrane AFC80 in a 1.2 m B1 membrane module is also provided for concentration control.

Pressure meters are provided between two membrane modules of AFC30 and behind the rearward membrane module.

FIG. 1 shows a flowsheet of the membrane separation apparatus.

The membrane separation apparatus BRO/BUF includes a pressure increase pump 4, a heat exchanger 5, a membrane module 6A (AFC80), a pressure meter 7, a membrane module 6B (AFC30), a membrane module 6C (AFC30), a pressure control valve 9 and a connection pipe connecting these components. With the circulating liquid pipe/hose 10, the circulating liquid through the pressure control valve 9 can be introduced in the circulating liquid tank. Also, the circulating liquid can be also introduced in another container for membrane cleaning and a sampling container.

The cleaning liquid storage tank 13 is a drum container having three base portions mutually connected by a pipe. Each container is connected with the pump 14 for cleaning liquid via a stop valve and with the pressure increase pump inlet pipe 3 via a valve. The containers store warm water of 40 to 55° C. An outlet of the pump for cleaning liquid is connected via a control valve to the hose which is used for introducing the cleaning liquid to the circulating liquid tank.

The permeate liquid in the membrane module 6B and the membrane module 6C is automatically weighed in time series by a scale 2 for the permeate liquid container. The permeate liquid can be introduced into a plastic container via the pipe/hose 16 for the permeate liquid from a top nozzle for the permeate liquid of the membrane module B or the membrane module C.

The circulatory system for normal operation of the membrane separation apparatus includes the circulating liquid tank 1, the pressure increase pump inlet pipe 3, the pressure increase pump 4, the heat exchanger 5, the membrane module A 6A, the membrane module B 6B, the membrane module C 6C, the pressure control valve 9 and pipes and hoses for connection of these components. For circulation of warm water, which will be described later, the circulating liquid tank is replaced by the container 11 for circulating warm-water membrane cleaning liquid.

The control panel 18 includes: a mechanism for regulating weight of the circulating liquid tank to keep the measurement value of weight of the circulating liquid tank 1 to a predetermined value; a mechanism for regulating temperature of the circulating liquid to control supply of water from a chiller water unit 19 so that the measurement value of temperature of the circulating liquid in the downstream of the pressure control valve 9 is regulated to a predetermined value; a mechanism for indicating total weight of the permeate liquid; a function to indicate the flow rate of the permeate liquid to calculate the flow rate of the permeate liquid based on a temporal change in the weight of the permeate liquid and on duration of time and to indicate the same; and a function to indicate the degree Brix of the circulating liquid to indicate the degree Brix in the downstream of the pressure control valve 9.

Operating Method and Process

The circulatory system of the apparatus is filled up with 0.5 wt % of enzyme detergent (ULTRASIL 53) at about 30° C. to conduct circulation cleaning of the apparatus. The detergent is then replaced by ion exchange water. Ion exchange water heated to about 50° C. is prepared in the container 11 for circulating warm-water membrane cleaning liquid. The warm water is made to circulate between the container 11 and the membrane separation apparatus. Additionally, after extracting the permeate liquid out of the system through the drain nozzle several times, both of the circulating liquid system and the permeate liquid system are made to circulate using the container 11 for circulating a warm-water membrane cleaning liquid. The circulating liquid system includes a container for circulating warm-water membrane cleaning liquid, a pump inlet pipe, a pressure increase pump, a heat exchanger, a membrane module A, a membrane module B, a membrane module C, a pressure control valve, a circulating liquid outlet pipe/hose and a container for circulating warm-water membrane cleaning liquid. The permeate liquid is extracted from permeate liquid side of the membrane modules B and C and circulated to the container for circulating warm-water membrane cleaning liquid via a hose. Thereby, the circulating liquid system and the permeate liquid system are possible to maintained at 50 to 53° C.

A polyglycerin mixture liquid containing 70 wt(s) % of water content at about 50° C. is prepared separately. The mixture liquid is diluted with heated ion exchange water and stirred to obtain 30 wt % of polyglycerin at about 50° C. is prepared in a circulating liquid tank.

Part of the warm water contained in the membrane separation apparatus of the circulatory system is extracted and replaced with the polyglycerin mixture liquid. The circulatory system is replaced with the polyglycerin liquid. The total amount of the permeate liquid is to be returned to the circulating liquid tank.

The initial operating pressure is set to 33 bars. The permeate liquid through the membrane AFC80 is removed from the system. The once-reduced concentration of the circulating liquid is made to increase to about 25%. Then, the total amount of the permeate liquid through the membrane AFC80 is returned to the circulating liquid tank 1. The permeate liquid through two membranes AFC30 is made to be discharged to a 20-liter container for the permeate liquid. The operation of the circulating liquid tank is continued at an operating temperature of 50 to 53° C. to keep the degree Brix of the circulating liquid to about 25%, which is the initial setting. While supplying ion exchange water heated to about 50° C. as diafiltration water to the circulating liquid tank, the permeate liquid through two membranes AFC30 is extracted out of the system. Inlet pressure of the module A is regulated manually by the pressure control valve so that the total flow rate of the permeate liquid becomes about 30 to 45 kg/hr. In the course of the process, the permeate liquid is sequentially discharged to a 20-liter container. The operation is continued such that the flow rate of the permeate liquid at the downstream module B is greater than half of the flow rate of the permeate liquid at the upstream module A. If the flow rate of the permeate liquid at the downstream module B becomes less than half of the flow rate of the permeate liquid at the upstream module A, the operating pressure may be increased or the operation concentration is decreased so as to keep the total permeate liquid and the flow rate of the permeate liquid of the module B, that is, of the downstream module A.

Diafiltration is continued with the degree Brix of the permeate liquid being measured. When the degree Brix of the permeate liquid becomes 0.6%, the operating pressure is reduced to 22 bars and the process is shifted to the latter stage.

In the latter stage, the operation is continued while keeping the flow rate of the permeate liquid at about 15 to 25 kg/hr. As in the former stage, the permeate liquid is sequentially discharged to a 20-liter container and the degree Brix of the circulating liquid is maintained at about 22%.

In this manner, the operation is continued until the degree Brix of the permeate liquid becomes 0.4%, where the operation of the membrane separation apparatus is stopped and, almost simultaneously, the supply of the diafiltration water is also stopped. Thereafter, the polyglycerin liquid, which is the residual liquid, is extracted from the circulating liquid tank. Obtained in the circulating liquid tank is a 27.3 kg of 22 wt %-equivalent polyglycerin liquid out of the initial 32.6 kg of 30 wt %-equivalent polyglycerin liquid. Analysis result of the obtained polyglycerin liquid is shown in Table 5 with the sample number C7. Subsequently, the polyglycerin liquid in the circulatory system is extruded out of the system from the membrane module via the circulating pump using warm water and then recovered.

As a result of the operation described above, 6.0 kg (as dry weight) of polyglycerin having a surface ratio to the internal standard substance shown in the C7 column in Table 5 is obtained out of 9.8 kg (as dry weight) of polyglycerin contained in the 14.8 kg of the material.

Table 6 shows tracked changes in the components of each sample based on the ratio of the surface ratio with respect to the internal standard substance of the circulating liquid sample to the initial surface ratio.

The progress index calculated as a ratio of the cumulative amount of the permeate liquid shown in Table 6 to the initial amount of the circulating liquid is 2.1, which indicates that glycerin content is reduced to less than one tenth of typical glycerin content. Diglycerin content is reduced to less than one tenth of typical diglycerin content with the progress index of 5.0.

And, the recovered product has glycerin content of less than measurement range, diglycerin content of less than one tenth of content, initially desired, diglycerin content, triglycerin content of less than half of content, initially desired, triglycerin content and the content of polyglycerins which is greater than that of tetraglycerin is increased.

In the above operation, the separation status index according to the present invention is the flow rate and the degree Brix of the permeate liquid. The progress index according to the present invention is the ratio of the amount of the permeate liquid to the initial amount of the circulating liquid. The flow rate of the permeate liquid is used also as the operating parameter. In particular, the operating pressure is first regulated using the flow rate of the permeate liquid as an index which indicates the separation status, while the amount of the permeate liquid serving as the separation status index such that the flow rate of the permeate liquid which is the operating parameter is maintained to a predetermined range of 30 to 45 kg/hr. After the degree Brix of the permeate liquid serving as the progress index is reduced to 0.6%, the flow rate of the permeate liquid, which is the operating parameter, is changed to a predetermined range of 15 to 25 kg/hr. The flow rate of the permeate liquid serving as the separation status index is regulated to the predetermined range by regulating the operating pressure and regulating a predetermined value of the concentration of the circulating liquid. After the degree Brix of the permeate liquid serving as the progress index reached to 0.4%, the separation refinement is completed.

The operating temperature is maintained here at the initially set temperature of 50 to 53° C. The operating parameter is not changed, but is maintained. Concentration of the circulating liquid is used as the operating parameter also when the flow rate of the permeate liquid of the downstream module B is maintained at half or more of that of the upstream module. In this operation, pH is not used as the operating parameter. Although the amount of the circulating liquid is not used as the operating parameter, the amount of the circulating liquid depends directly on the change in the concentration of the circulating liquid. The amount of the circulating liquid may therefore be considered as the operating parameter. That is, increase in concentration means decrease in amount of the circulating liquid. Accordingly, the amount of the circulating liquid is, similarly, applicable as in the concentration of the circulating liquid.

Also, although the flow rate of the permeate liquid is used here as the operating parameter or the separation status index, the present invention is not limited thereto. The operating parameter can also used only the upstream or downstream module, the sum thereof, or the permeation flux obtained by dividing the module(s) by the area of the used separation membrane.

Furthermore, since the degree Brix value of the circulating liquid here varies in a small range of 22 to 25%, the degree Brix of the permeate liquid is used as the progress index or the separation status index. It is advantageous, however, to use a degree Brix ratio, which is obtained by dividing the degree Brix of the permeate liquid by the degree Brix of the circulating liquid, in accurate detection of the state of the circulating liquid and the state of the membrane separation.

TABLE 4

| | PERMEATE LIQUID | | | CIRCULATING LIQUID | | | | |
|---|---|---|---|---|---|---|---|---|
| | TOTAL | | AVERAGE | | | | | |
| | PERMEATE LIQUID/INITIAL LIQUID | DEGREE BRIX % | FLOW RATE OF PERMEATE LIQUID | DEGREE BRIX % | pH | TEMPERATURE °C. | PRESSURE METER Bar | PRESSURE METER Bar |
| kg | | | | | | | | |
| START | | | KG/M2/HR | 24.9 | 4.2 | | | |
| 1-PB 22.4 | | 3.0 | | | | | | |
| 1-PC 15.3 | 1.0 | 5.1 | 38 | 24.6 | 4.2 | 52 | 30 | 27 |
| 4-PB 19.1 | | 0.6 | | | | | | |
| 4-PC 10.5 | 4.0 | 0.6 | 33 | 24.2 | 4.2 | 51 | 32 | 30 |
| 5-PB 22.3 | | 0.6 | | | | | | |
| 5-PC 8.7 | 5.0 | 1.2 | 17 | 22.6 | 4.2 | 52 | 21 | 18 |
| 7-PB 10.7 | | 0.4 | | | | | | |
| 7-PC 5.8 | 6.3 | 0.8 | 18 | 22.3 | 4.3 | 52 | 23 | 20.5 |

TABLE 5

| | SAMPLE NO. | | | | |
|---|---|---|---|---|---|
| | C0 | C1 | C4 | C5 | C7 |
| | TOTAL PERMEATE LIQUIDS/INITIAL VOLUME | | | | |
| | START | 1.0 | 4.0 | 5.0 | 6.3 |
| MONO G1 | 0.578 | 0.106 | 0.000 | 0.000 | 0.000 |
| DI G2 | 1.274 | 0.972 | 0.210 | 0.139 | 0.000 |
| TRI G3 | 0.962 | 1.027 | 0.590 | 0.559 | 0.391 |
| TETRA G4 | 0.669 | 0.792 | 0.755 | 0.805 | 0.819 |
| PENTA G5 | 0.700 | 0.820 | 0.771 | 0.863 | 0.900 |

TABLE 6

| | SAMPLE NO. | | | | |
|---|---|---|---|---|---|
| | C0 | C1 | C4 | C5 | C7 |
| | TOTAL PERMEATE LIQUIDS/INITIAL VOLUME | | | | |
| | START | 1.0 | 4.0 | 5.0 | 6.3 |
| MONO G1 | 1.000 | 0.161 | 0.000 | 0.000 | 0.000 |
| DI G2 | 1.000 | 0.668 | 0.150 | 0.067 | 0.000 |
| TRI G3 | 1.000 | 0.935 | 0.560 | 0.359 | 0.258 |
| TETRA G4 | 1.000 | 1.037 | 1.031 | 0.743 | 0.778 |
| PENTA G5 | 1.000 | 1.025 | 1.005 | 0.761 | 0.816 |

Next, the above system will be further described.

Figure 5:
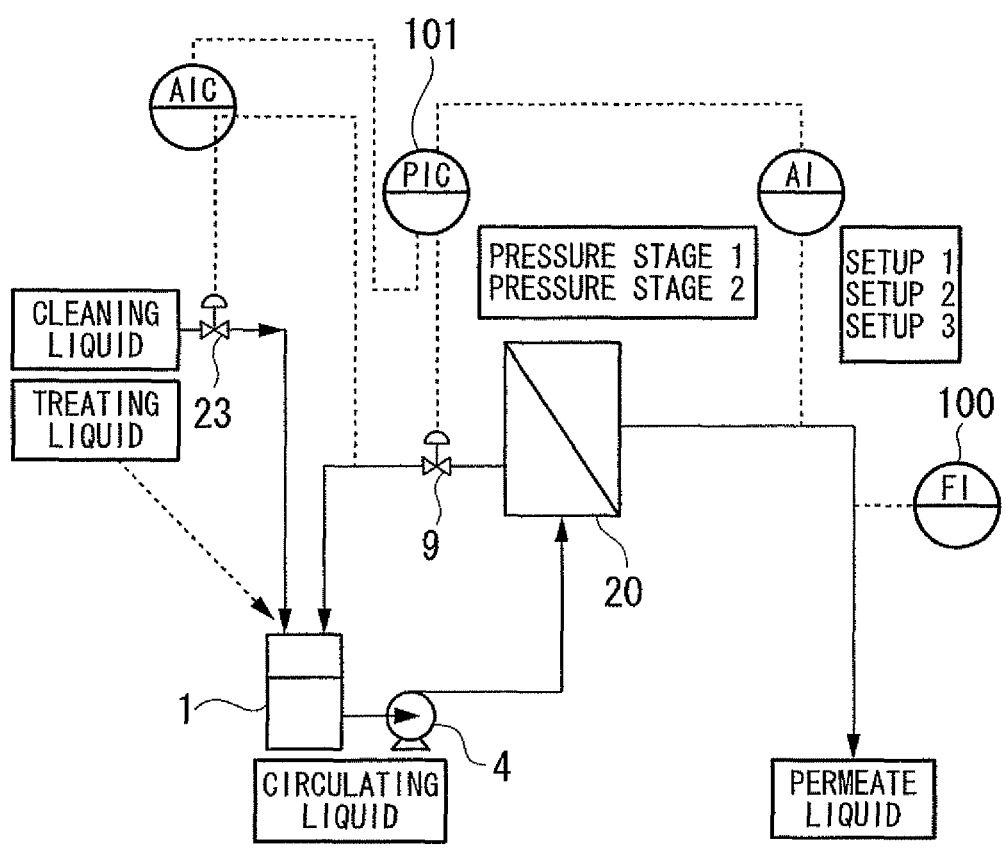
FIG. 5 illustrates a configuration of a separation system according to another embodiment (i.e., a first embodiment).

FIG. 5 illustrates a configuration of a separation system according to another embodiment (i.e., a first embodiment). Components having the same function as those shown in FIG. 1 are given the same reference numerals, and repeated descriptions thereof will be omitted. A permeate liquid flow meter 100 measures the flow rate of the permeate liquid fractionated by a membrane separation apparatus 20 and discharged therefrom. A pressure meter 101 measures the operating pressure of the membrane module of the membrane separation apparatus 20. The operating pressure of the membrane separation apparatus 20 is regulated by the pressure control valve 9.

Figure 6:
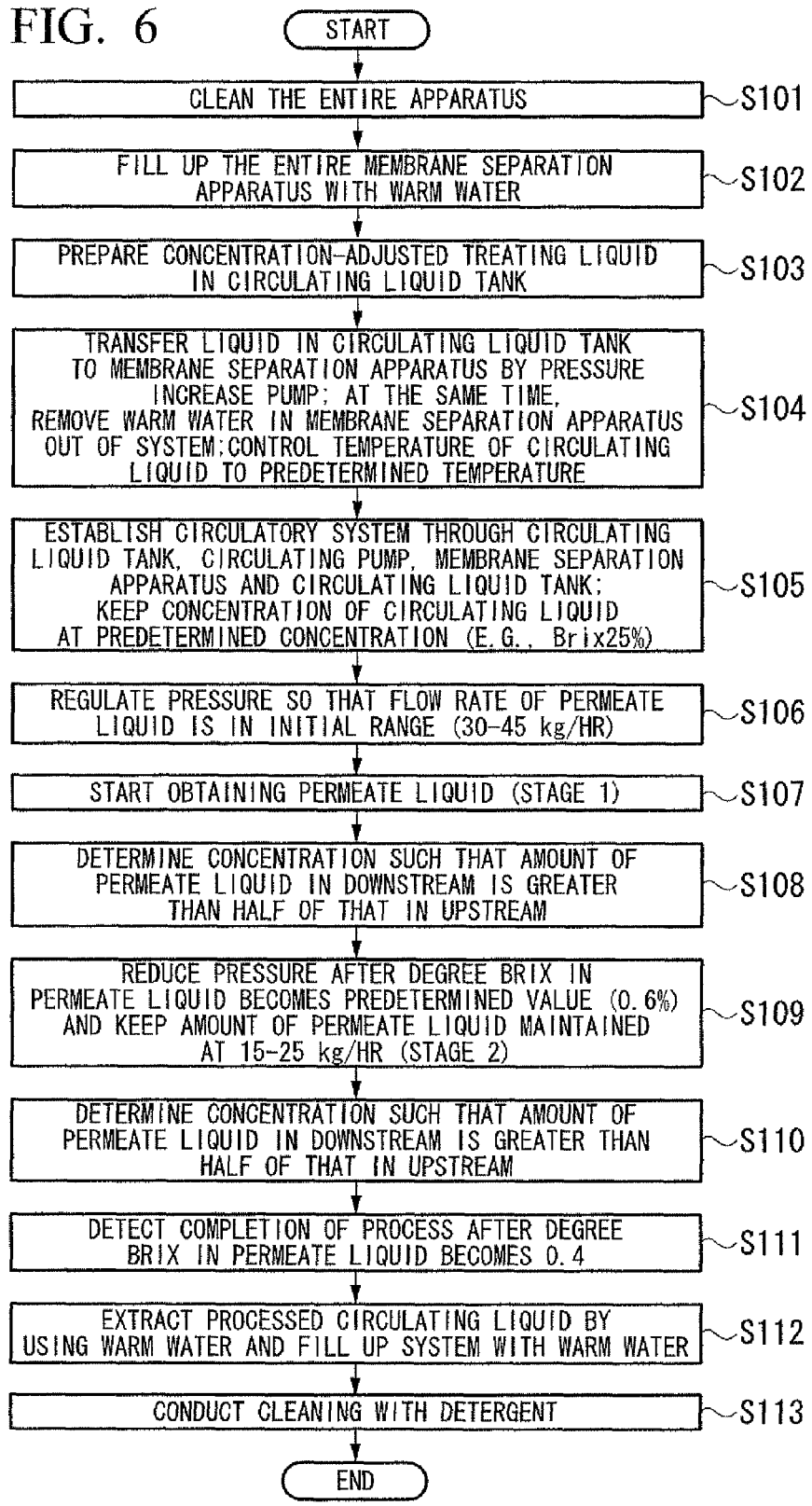
FIG. 6 is a flowchart illustrating an operation sequence of the separation system.

Next, an operation of a separation system shown in FIG. 5 will be described. FIG. 6 is a flowchart illustrating an operation sequence of the separation system.

First, the entire apparatus is cleaned (step S101). The membrane separation apparatus is then filled up with warm water (step S102). A concentration-adjusted treating liquid is prepared in a circulating liquid tank (step S103).

A liquid in the circulating liquid tank is transferred to the membrane separation apparatus by a pressure increase pump. At the same time, the warm water in the membrane separation apparatus is removed out of the system so that the temperature of the circulating liquid is controlled to a predetermined temperature (step S104).

A circulatory system through a circulating liquid tank, a circulating pump, a membrane separation apparatus and a circulating liquid tank is established. Concentration of the circulating liquid is maintained at the predetermined concentration (e.g., Brix 25%) by circulating the permeate liquid with predetermined operating pressure (step S105). Pressure is regulated so that the flow rate of the permeate liquid is in the initial range (30 to 45 kg/hr) (step S106). Diafiltration (stage 1) is started by supplying the cleaning liquid and obtaining the permeate liquid (step S107). Concentration here is determined such that, for example, the amount of the permeate liquid in the downstream is greater than half of that in the upstream (step S108).

Pressure is reduced after the degree Brix in the permeate liquid becomes a predetermined value (e.g., 0.6%) and the amount of the permeate liquid is maintained at about 15 to 25 kg/hr (stage 2) (step S109). Concentration of the permeate liquid here is determined such that, for example, the amount of the permeate liquid in the downstream is greater than half of that in the upstream (step S110).

And when the degree Brix in the permeate liquid becomes 04%, completion of the process is detected (step S111). The processed circulating liquid is extracted by using warm water and the system is filled with the warm water (step S112). Cleaning with detergent is then conducted (step S113).

Figure 7:
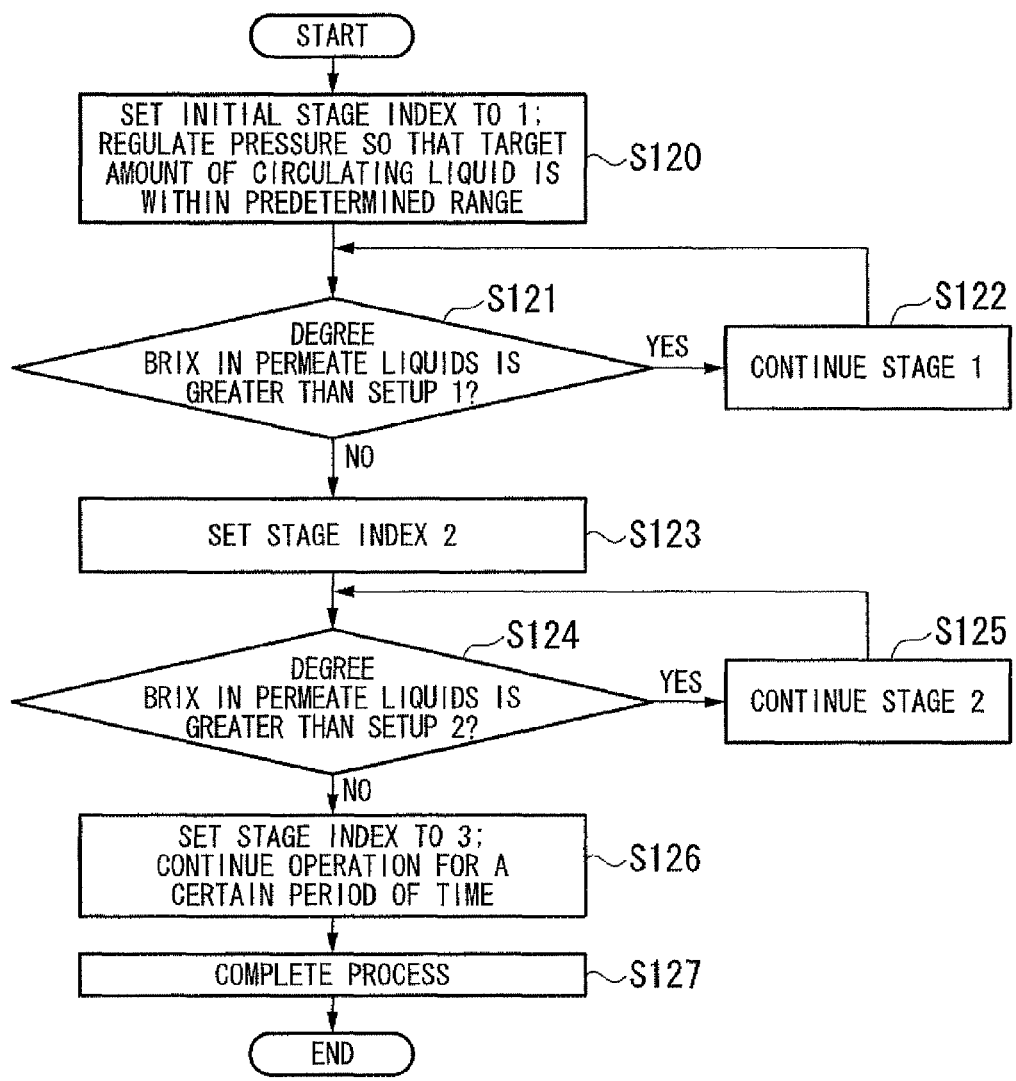
FIG. 7 is a flowchart illustrating control on progress in stages in the separation system shown in FIG. 5.

Next, control on progress in stages in the separation system of FIG. 5 will be described with reference to the flowchart of FIG. 7.

An initial stage index is set to 1. The pressure is regulated by the pressure control valve 9 so that a target amount of the circulating liquid is within a predetermined range (step S120). It is then determined whether or not the degree Brix in the permeate liquids is greater than setup 1 (step S121). If affirmative in step S121, the stage 1 is continued and the routine proceeds to step S121 (step S122). On the other hand, If negative in step S121, the stage index is set to 2 (step S123). It is determined whether or not the degree Brix in the permeate liquids is greater than setup 2 (step S124). If affirmative in step S124, the pressure stage 2 is continued (step S125) and the routine proceeds to step S124. If negative in step S124, the stage index is set to 3 and the operation is continued for a certain period of time (step S126). Then, the process is completed (step S127).

Figure 8:
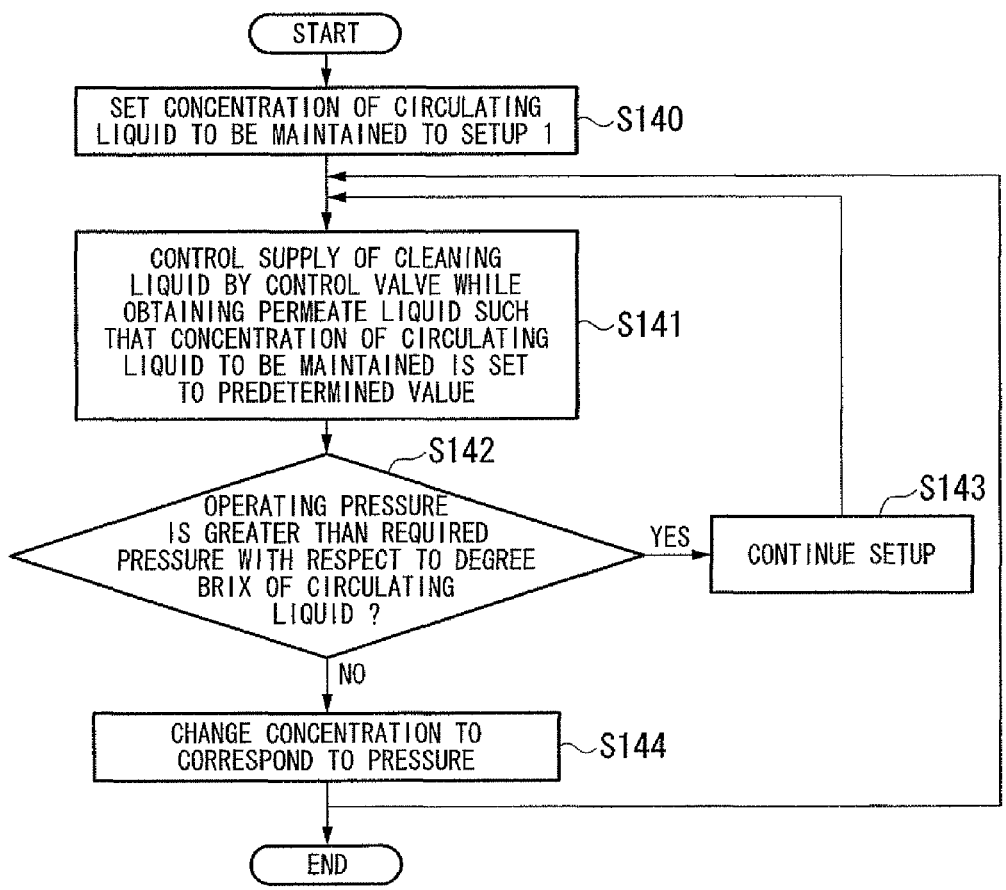
FIG. 8 is a flowchart illustrating control on concentration of a circulating liquid in the separation system shown in FIG. 5.

Next, control on concentration of the circulating liquid in the separation system of FIG. 5 will be described with reference to the flowchart of FIG. 8.

The concentration of the circulating liquid to be maintained is set to setup 1 (step S140). The supply of the cleaning liquid is controlled by a control valve while obtaining the permeate liquid such that the supply of the cleaning liquid is controlled to setup 1 which is a predetermined concentration of the circulating liquid (step S141). It is then determined whether or not the operating pressure is greater than the required pressure with respect to the degree Brix of the circulating liquid (step S142). If affirmative in step S142, the routine proceeds to step S141. If negative in step S142, concentration is changed to correspond to the pressure (step S144), and the routine proceeds to step S141.

Figure 9A:
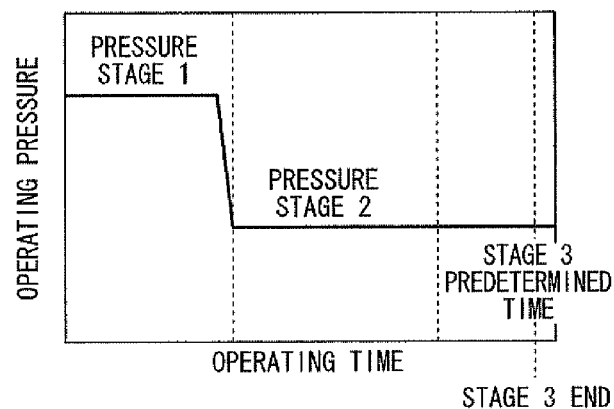
FIG. 9A illustrates variation in operating pressure in the separation system shown in FIG. 5.
Figure 9B:
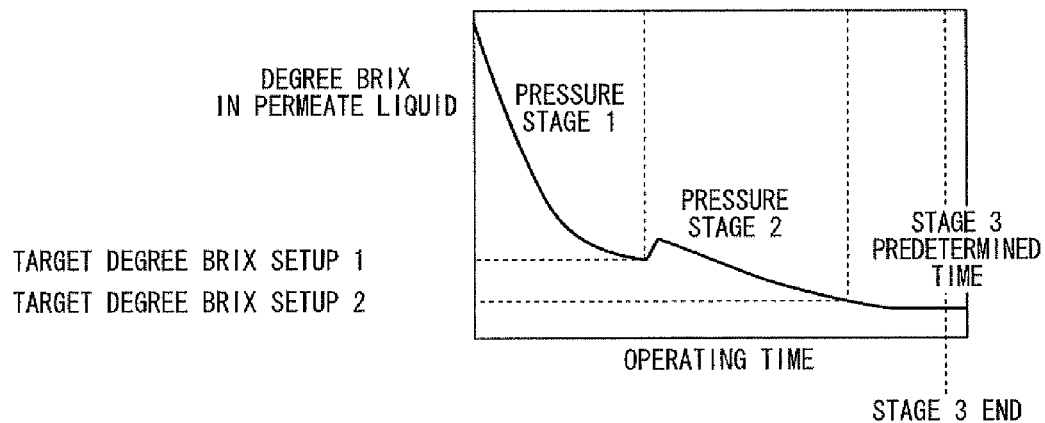
FIG. 9B illustrates variation in degree Brix in a permeate liquid in the separation system shown in FIG. 5.

Next, variation in the degree Brix in the permeate liquid during the processes shown in FIGS. 6 to 8 in the separation system of FIG. 5 will be described with reference to FIGS. 9A and 9B. In FIG. 9A, the operating pressure is plotted along vertical axis and the operating time is plotted along the horizontal axis. In FIG. 9B, the degree Brix in the permeate liquid is plotted along the vertical axis and the operating time is plotted along the horizontal axis.

While the operating pressure is maintained at 'pressure stage 1' (FIG. 9A), membrane separation is conducted until the predetermined value of the target degree Brix in the degree Brix in the permeate liquid reaches 'setup 1' (FIG. 9B). When the degree Brix in the permeate liquid reaches the predetermined value 1 of the target degree Brix (FIG. 9A), the operating pressure is set to the pressure stage 2. After the operating pressure is switched to 'setup 2', the measurement value of the degree Brix in the permeate liquid temporarily increases and then gradually decreases toward 'setup 2', which is the predetermined value of the target degree Brix. And, the membrane separation is completed when, or after a certain period of time that, the degree Brix in the permeate liquid reaches the predetermined value 2 of the target degree Brix.

Figure 10:
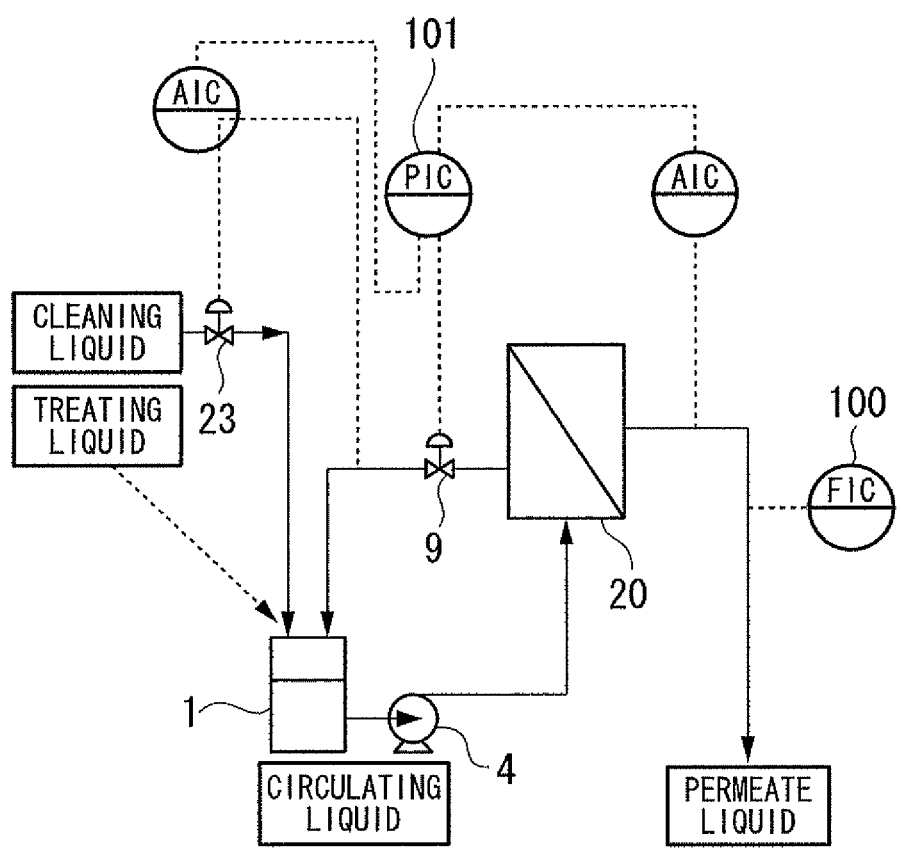
FIG. 10 illustrates a configuration of a separation system according to a second embodiment.

Next, a separation system according to a second embodiment will be described. FIG. 10 illustrates a configuration of the separation system according to the second embodiment. Components having the same function as those shown in FIG. 5 are given the same reference numerals, and a repeated description thereof will be omitted.

Figure 11:
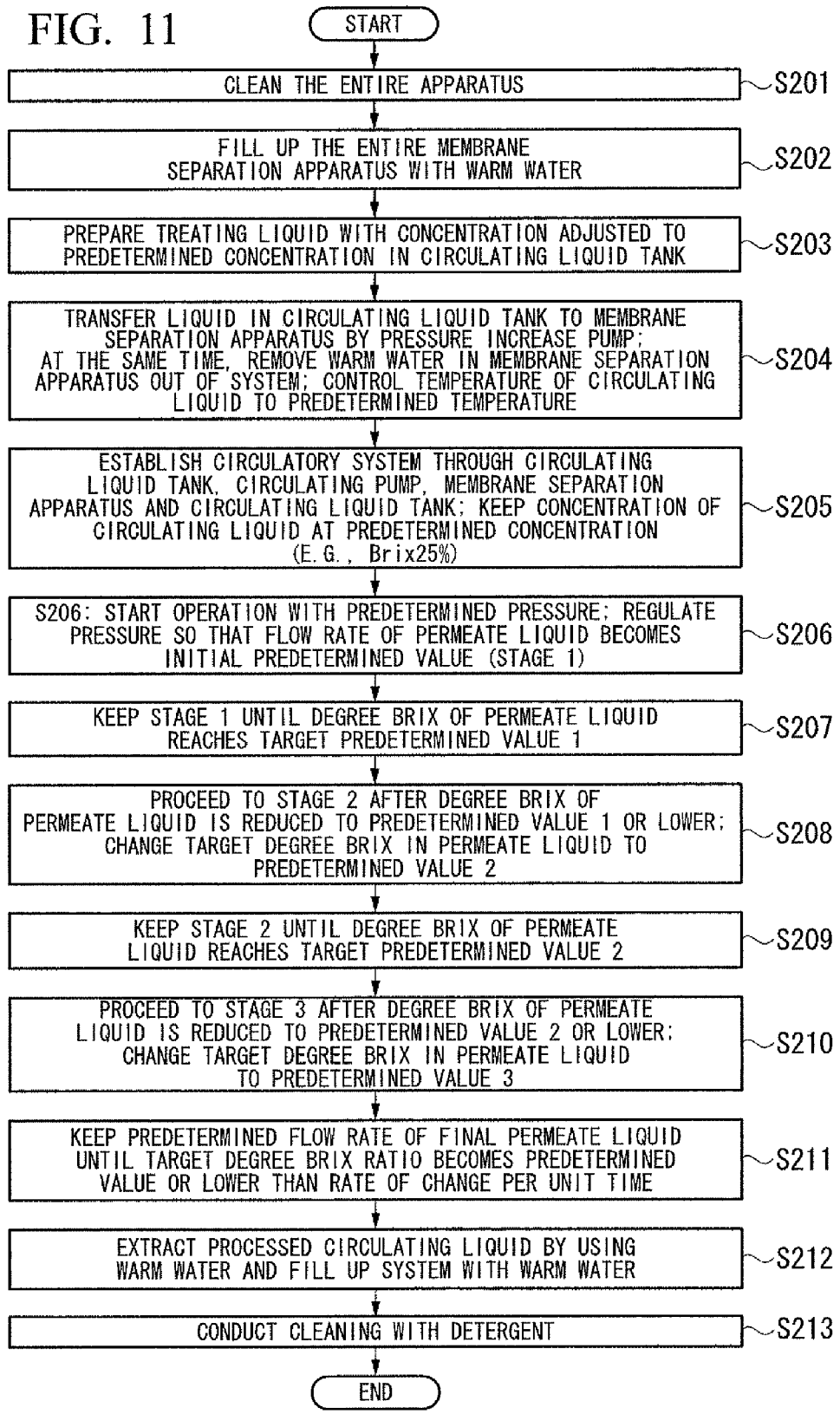
FIG. 11 is a flowchart illustrating an operation sequence of the separation system according to the second embodiment.

Next, an operation of the separation system shown in FIG. 10 will be described. FIG. 11 is a flowchart illustrating an operation sequence of the separation system according to the present embodiment.

First, the entire apparatus is cleaned (step S201). The membrane separation apparatus is then filled with warm water (step S202). A concentration-adjusted treating liquid is prepared in a circulating liquid tank (step S203).

A liquid in the circulating liquid tank is transferred to the membrane separation apparatus by a pressure increase pump. At the same time, the warm water in the membrane separation apparatus is removed out of the system so that the temperature of the circulating liquid is controlled to a predetermined temperature (step S204).

A circulatory system through a circulating liquid tank, a circulating pump, a membrane separation apparatus and a circulating liquid tank is established. Concentration of the circulating liquid is maintained at the predetermined concentration (e.g., Brix 25%) (step S205). Here, after the operation is started with a predetermined pressure of the pressure control valve 9. Then, the pressure is thereafter regulated so that the flow rate of the permeate liquid becomes an initial predetermined value or within a predetermined range (stage 1, step S206). And, the regulated pressure is maintained until the degree Brix or the degree Brix ratio of the permeate liquid reaches the target predetermined value 1 (step S207). And, when the degree Brix or the degree Brix ratio of the permeate liquid is reduced to the predetermined value 1 or lower, the pressure stage proceeds to stage 2. The predetermined values of the flow rate of the permeate liquid or the operating pressure are determined accordingly (step S208).

After the degree Brix in the permeate liquid reaches the predetermined value 2 or lower, the pressure stage proceeds to stage 3 (stage i+1). In this process, sequential progress is made in the pressure stage while the concentration of the circulating liquid is maintained to the value suitable for the operating pressure (step S210).

And then, the predetermined amount of the final permeate liquid is maintained until the target degree Brix ratio becomes a predetermined value, until the target degree Brix ratio becomes lower than the rate of change per unit time, or after a certain period of time after the target degree Brix ratio is reached (step S211). And, the processed circulating liquid is extracted by using warm water and the system is filled up with the warm water (step S212). Cleaning with detergent is then conducted (step S213).

Figure 12:
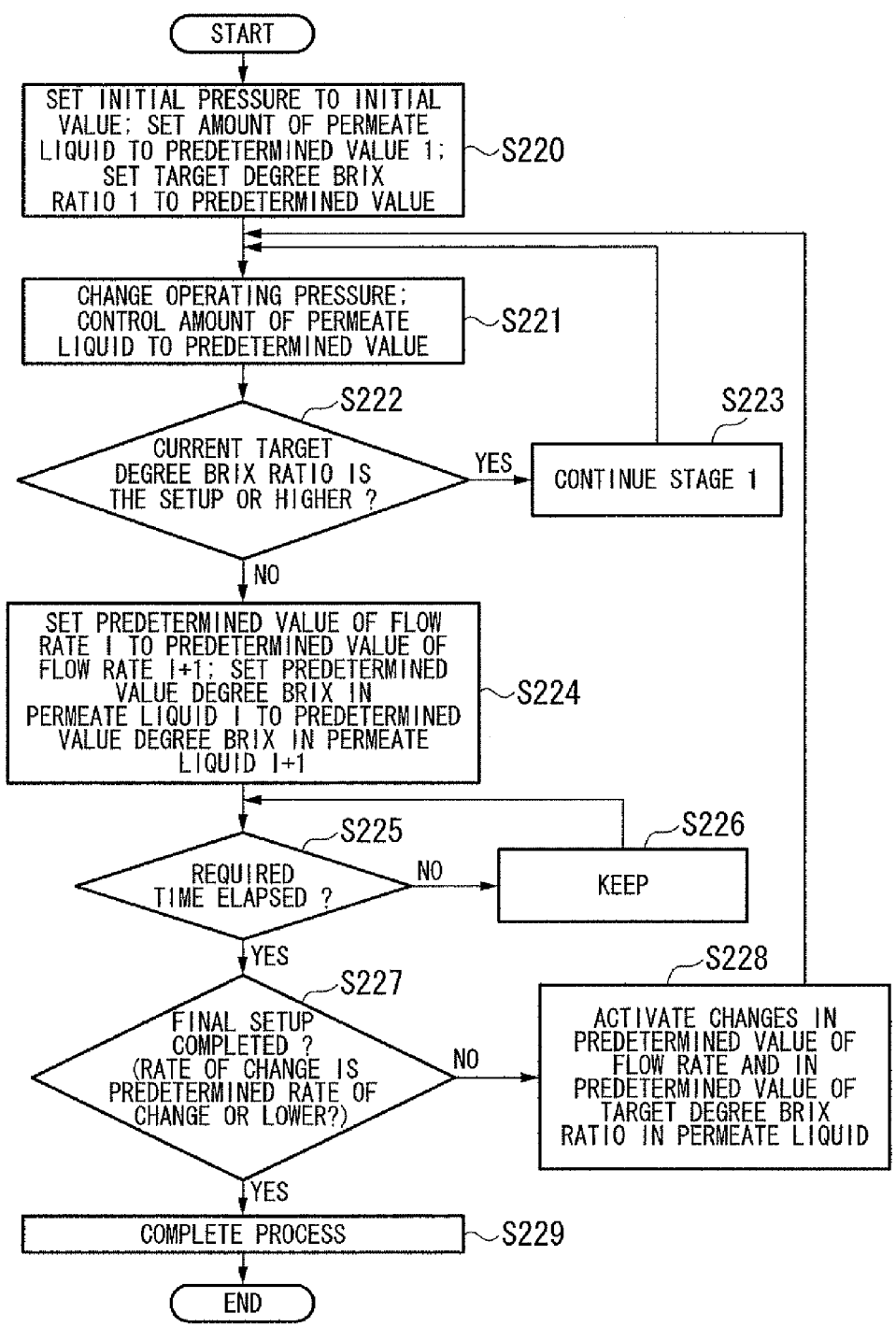
FIG. 12 is a flowchart illustrating control on progress in stages in the separation system shown in FIG. 10.

Next, control on progress in stages in the separation system of FIG. 10 will be described with reference to the flowchart of FIG. 12.

Initial pressure after the startup is set to an initial value. The amount of the permeate liquid is set to the predetermined value 1 and the target degree Brix ratio 1 is set to the predetermined value (step S220). And, the operating pressure is then changed such that the amount of the permeate liquid is controlled to the predetermined value (step S221). And, it is then determined whether or not the current target degree Brix ratio is hither than the ratio in the setup (step S222). If affirmative in step S222, stage 1 is continued and the routine proceeds to step S221 (step S223). On the other hand, if negative in step S222, i.e., if the current target degree Brix ratio is lower than the ratio in the setup, the predetermined value for the flow rate is made to advance by 1 to be (i+1) and the predetermined value of the degree Brix in the permeate liquid is made to advance by 1 to be (i+1) (step S224).

And, It is then determined whether or not the required time has elapsed (step S225). If negative in step S225, the predetermined values are maintained (step S226) and the routine proceeds to step S225.

On the other hand, If affirmative in step S225, it is then determined whether or not the final setup has completed, i.e., whether or not the rate of change is the predetermined rate of change or lower (step S227). If negative in step S227, changes in the predetermined value of the flow rate and in the predetermined value of the target degree Brix ratio in the permeate liquid are activated (step S228) and the routine proceeds to step S221. If affirmative in step S227, the process is completed (step S229).

Figure 13:
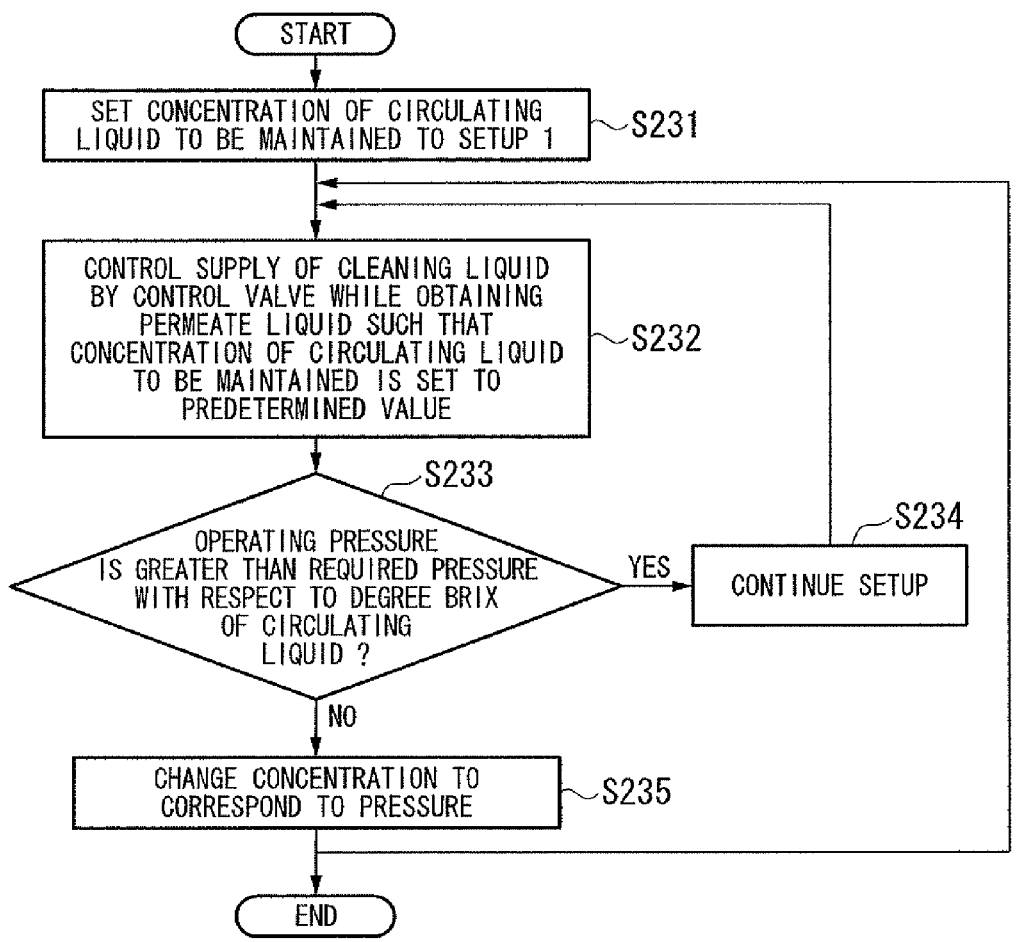
FIG. 13 is a flowchart illustrating control on concentration of a circulating liquid in the separation system of FIG. 10.

Next, control on concentration of the circulating liquid in the separation system of FIG. 10 will be described with reference to the flowchart of FIG. 13.

The concentration of the circulating liquid to be maintained is set to 'setup 1' (step S231). The supply of the cleaning liquid is controlled by a control valve while obtaining the permeate liquid such that the supply of the cleaning liquid is controlled to 'setup 1' which is a predetermined concentration of the circulating liquid (step S232). And then, It is determined whether or not the operating pressure is greater than the required pressure with respect to the degree Brix of the circulating liquid (step S233). If affirmative in step S233, the routine proceeds to step S232. If negative in step S233, concentration is changed to correspond to the pressure (step S235), and the routine proceeds to step S232.

Next, variation in the degree Brix in the permeate liquid during the processes shown in FIGS. 11 to 13 in the separation system of FIG. 10 will be described with reference to FIGS. 14A and 14B.

Figure 14:
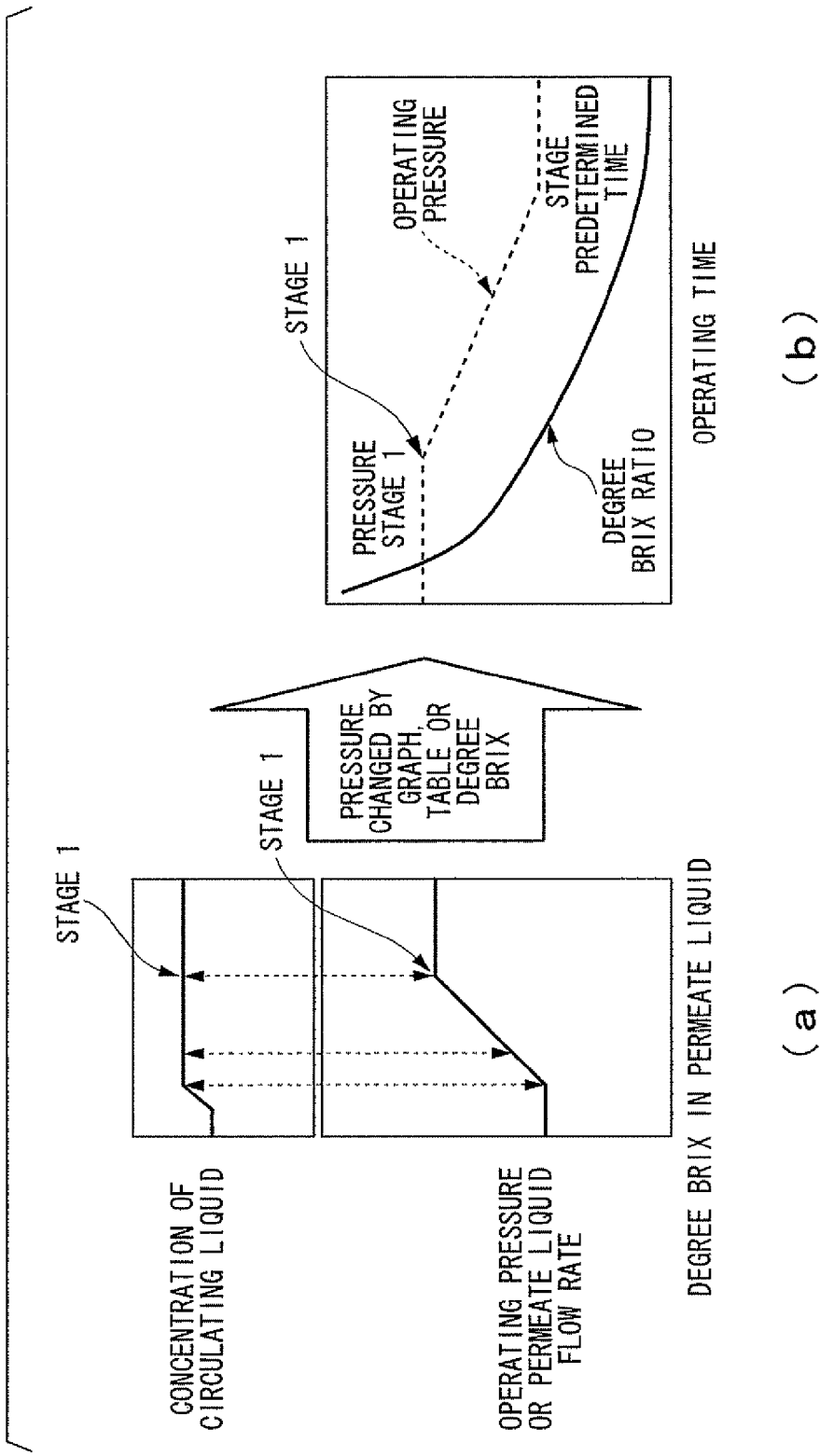
FIG. 14 illustrates variation in degree Brix in a permeate liquid in the separation system shown in FIG. 10.

In the upper graph of FIG. 14A, the concentration of the circulating liquid is plotted along the vertical axis and the degree Brix in the permeate liquid is plotted along the horizontal axis. In the lower graph of FIG. 14A, the operating pressure (or the flow rate of the permeate liquid) is plotted along the vertical axis and the degree Brix in the permeate liquid is plotted along the horizontal axis. In FIG. 14B, the degree Brix ratio is plotted along the vertical axis and the operating time is plotted along the horizontal axis.

After the operation is started, the operating pressure is maintained at the initial value for a certain period of time and then decreased gradually. When the operating pressure reaches the predetermined value of the second stage of the operating pressure, the pressure is maintained for a certain period of time. If the operating pressure is changed rapidly to the predetermined value of the second stage, fractionation proceeds with values different from the target value especially in the concentration of the target substance. According to the present embodiment, however, since the operating pressure is controlled to decrease gradually, fractionation is able to be conducted with values close to the target value especially in the concentration of the target substance.

Figure 15:
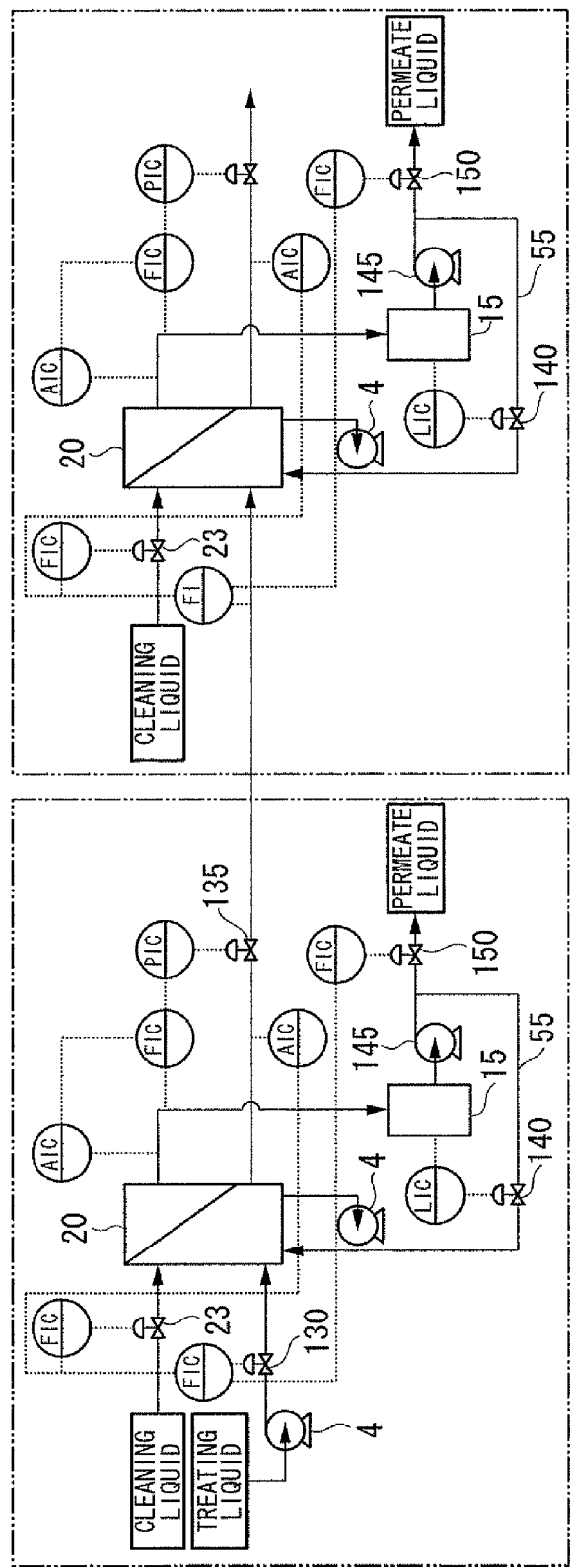
FIG. 15 illustrates a configuration of a separation system according to a third embodiment.

Next, a separation system according to a third embodiment will be described. FIG. 15 illustrates a configuration of the separation system according to the third embodiment. In the present embodiment, multiple separation systems shown, for example, in FIG. 5 are provided in multiple stages. In FIG. 15, components having the same function as those shown in FIG. 5 are given the same reference numerals, and repeated descriptions thereof will be omitted.

In FIG. 15, a flow control valve 130 regulates the amount of an treating liquid supplied to a membrane separation apparatus 20. A flow control valve 135 is provided between an upstream membrane separation apparatus 20 and a downstream membrane separation apparatus 20 so as to regulate the partial amount of the treating liquid in the upstream membrane separation apparatus 20 supplied to the downstream membrane separation apparatus 20.

A pump 145 feeds a permeate liquid stored in a permeate liquid container 15 toward the membrane separation apparatus 20. A flow control valve 140 is provided between the pump 145 and the membrane separation apparatus 20 so as to regulate a flow rate of the permeate liquid (i.e., a return permeate liquid 55) which flows into the membrane separation apparatus 20 from the permeate liquid container 15. A flow control valve 150 is provided in a path branched from a pipe connecting the pump 145 to the membrane separation apparatus 20 through which the liquid is extracted as the permeate liquid. The flow control valve 150 regulates the amount of the permeate liquid being extracted.

An operating method, of the separation system in a substantially normal state in FIG. 15 will be described. The left half represents a first-stage separation system and the right half is a second-stage separation system. The third-stage and thereafter is connected to the all-stage in the same manner as that of the second-stage separation system.

First, a cleaning liquid is introduced in proportion to the supply flow rate of treating liquid to the first stage. The permeate liquid is extracted. Part of the circulating liquid is transferred to the subsequent stage by the control of the operating pressure. The permeation flow rate here is used to control permeability. This is because the flux and the amount of the permeate liquid relates directly to the separativity. The operation proceeds with a liquid amount defined such that a to-be-discharged amount of the permeate liquid in the permeate liquid from the membrane separation apparatus is extracted from the system and the rest of the liquid is recycled in the circulatory system.

Here, it able to be considered that, the concentration, such as the degree Brix ratio of the permeate liquid, may be controlled. In this case, a measured degree Brix in the permeate liquid or a degree Brix ratio obtained by dividing the degree Brix in the permeate liquid by the degree Brix in the circulating liquid serves as the separation status index. In order to regulate the separation status index, the amount of the permeate liquid or the operating pressure may be controlled.

The concentration of the circulating liquid is varied depending directly on a relationship between concentration and a flow rate of each of the liquids, including the treating liquid and the cleaning liquid supplied to the system, the circulating liquid transferred to the subsequent stage and the permeate liquid discharged out of the system. The concentration of the circulating liquid can be controlled by determining the flow rate for each liquid and, in some cases, by the concentration of the circulating liquid. In the system shown in FIG. 15, it is considered that the concentration of the circulating liquid is controlled by the flow rate of the cleaning liquid, a flow ratio of the permeate liquid to the circulating liquid, or the amount of supplied treating liquid.

Operating Parameters

In the flowsheet shown in FIG. 15, control units for operating pressure, concentration of the circulating liquid and the amount of the permeate liquid are provided as the operating parameters for permeability. In addition, a heat exchanger can be provided to control the operating temperature, a pH controller can be provided for pH control or a circulating liquid flow rate sensor can be provided to control the flow rate of the circulating liquid.

Separation Status Index

The amount of the permeate liquid, the degree Brix and the degree Brix ratio indicate the separation status, and a unit to handle them is specified in the system of FIG. 15. That is, a greater degree Brix of the permeate liquid indicates a higher permeability of the permeate liquid as an fractionation trend. A greater flow rate of the permeation liquid indicates a lower permeability of the permeate liquid.

Progress Index

Also, the progress can be represented in terms of the degree Brix of the permeate liquid. In the system of FIG. 15, under the same condition of the flow rate of the permeate liquid, the downstream stage usually has the smaller progress index because of the decreased pressure caused by pressure loss. The degree Brix and the degree Brix ratio in each flow rate of the permeate liquids serve as progress indices.

Separation Status Index and Progress Index in Continuous Multistage Process

Although it is difficult to clearly distinguish the separation status index from the progress index in the multistage process, it is considered for the inventors of the present invention as follows: the separation status index may be used for determination whether or not the separation status at the stage is normal or whether or not a liquid is highly permeable. Also, the progress index can be used to indicate the degree of separation progress in the entire apparatus although the separation status of each stage may determined by the same index as the separation status index.

Note that, in the continuous process in which a separation process is continued while keeping the supply flow rate of the material or the flow rate of the permeate liquid in the steady state, the processes, such as a process of the amount of the materials, temporarily proceeds. It is difficult to indicate progress in refinement by an index of temporal progress/the progress index because the entire control of the operation is basically for the maintenance of the steady state. Measurement values, such as the degree Brix ratio of the permeate liquid indicate a degree of achievement in the required separation. For example, in a three-stage operation, each stage is provided with a degree of target achievement, such as, a "degree 1" of achievement for the first stage, a "degree 2" of achievement for the second stage and a "degree 3" of achievement for the third stage. The operating parameters may be controlled using, as the progress index, the degree of achievement which progresses as stage proceeds. That is, if it is determined that the actual process is behind the progress index, conditions to increase permeability may be selected. Such conditions may include conditions with higher temperature or conditions in which the return permeate liquid in the circulatory system is decreased with lower operation pressure. If it is determined, on the other hand, that the actual process is advanced the progress index, conditions to decrease permeability may be selected. Such conditions may include conditions with lower temperature or conditions with higher pressure. In this manner, the progress index is able to be achieved state to be kept stable.

Figure 16:
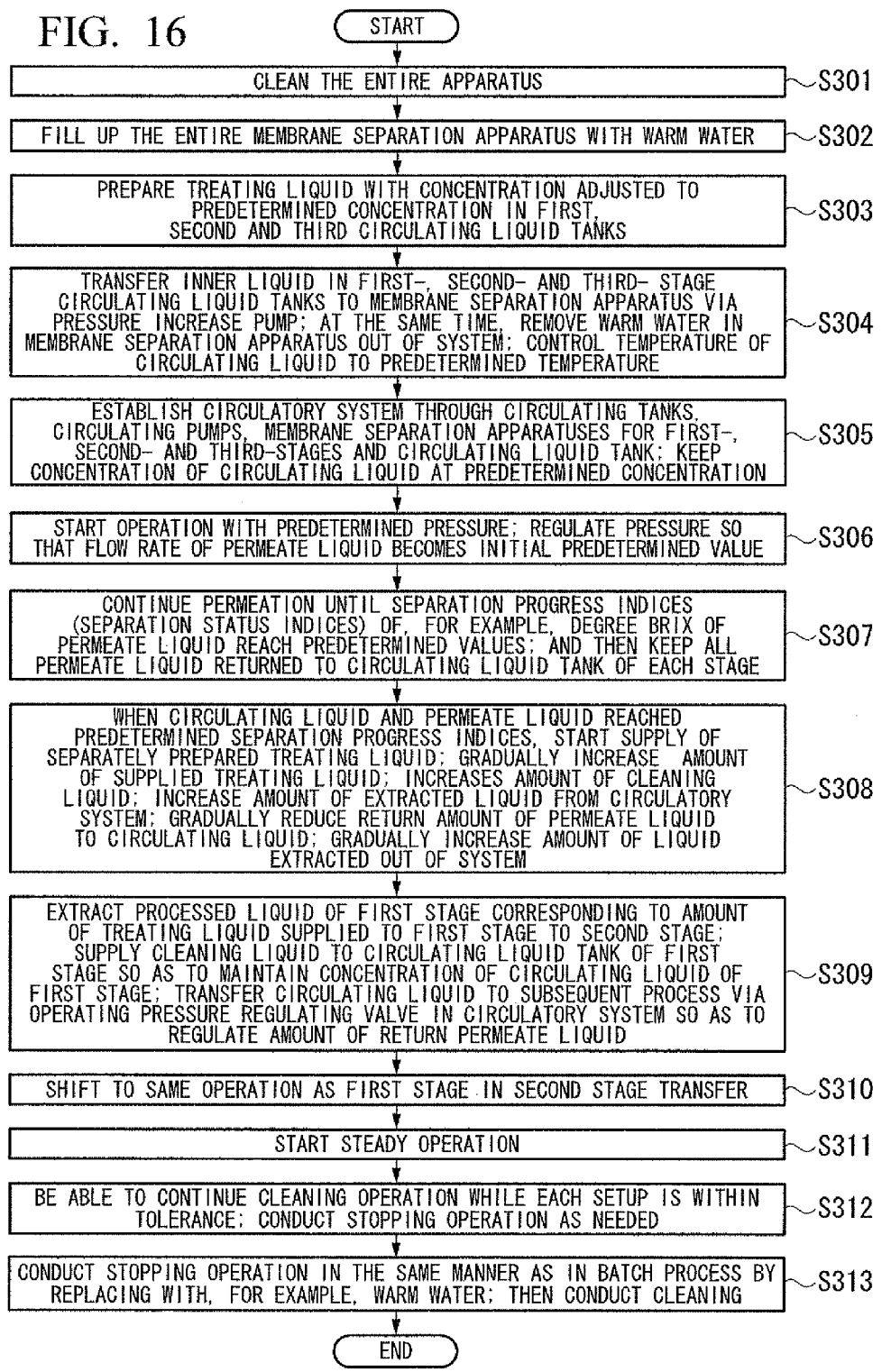
FIG. 16 is a flowchart illustrating an operation sequence of the separation system according to the third embodiment.

Next, operation of the separation system shown in FIG. 15 will be described. FIG. 16 is a flowchart illustrating an operation sequence for the separation system according to the present embodiment.

First, the entire apparatus is cleaned (step S301). The entire membrane separation apparatus is then filled up with warm water (step S302). A concentration-adjusted treating liquid is prepared in the first, second and third circulating liquid tanks (step S303).

The inner liquid in the first-, second- and third-stage circulating liquid tanks is transferred to the membrane separation apparatus via a pressure increase pump. Warm water in the membrane separation apparatus is removed out of the system and the temperature of the circulating liquid is controlled to a predetermined temperature (step S304).

A circulatory system is established through circulating tanks, circulating pumps, membrane separation apparatuses for the first-, second- and third-stages and a circulating liquid tank. Concentration of the circulating liquid is maintained at the predetermined concentration (step S305). Here, the operation is started with the pressure of the pressure control valve 9 being a predetermined pressure. The pressure is thereafter regulated so that the flow rate of the permeate liquid becomes an initial predetermined value or within a predetermined range (step S306). The permeation is continued until separation progress indices (i.e., separation status indices) of, for example, the permeate liquid reach the predetermined values 1, 2 and 3. When the indices reach the predetermined values, the state (whole circulation) in which all of the permeate liquid is returned to the circulating liquid tank of each stage is maintained (step S307). When the circulating liquid and the permeate liquid reached the predetermined separation progress indices, supply of the separately prepared treating liquid is started. The amount of supplied treating liquid is gradually increased and, at the same time, the amount of the cleaning liquid is also increased. The amount of extracted liquid from the circulatory system is also increased. The return amount of the permeate liquid to the circulating liquid is reduced gradually and the amount of liquid extracted out of the system is increased gradually (step S308).

A processed liquid of the first stage corresponding to the amount of the treating liquid supplied to the first stage is extracted to the second stage. The cleaning liquid is supplied to the circulating liquid tank of the first stage so as to maintain concentration of the circulating liquid of the first stage. The circulating liquid is transferred to the subsequent process via an operating pressure control valve in the circulatory system so as to regulate the amount of the return permeate liquid 55 (step S309). And the same operation is conducted in the membrane separation apparatus 20 of the second stage and thereafter (step S310).

Then, a steady operation is conducted (step S311). A cleaning operation is continued while each of the setups is within tolerance. A stopping operation is conducted as needed (step S312). The stopping operation here is conducted in the same manner as in the batch process by changing to, for example, warm water. Cleaning is then conducted (step S313).

Figure 17:
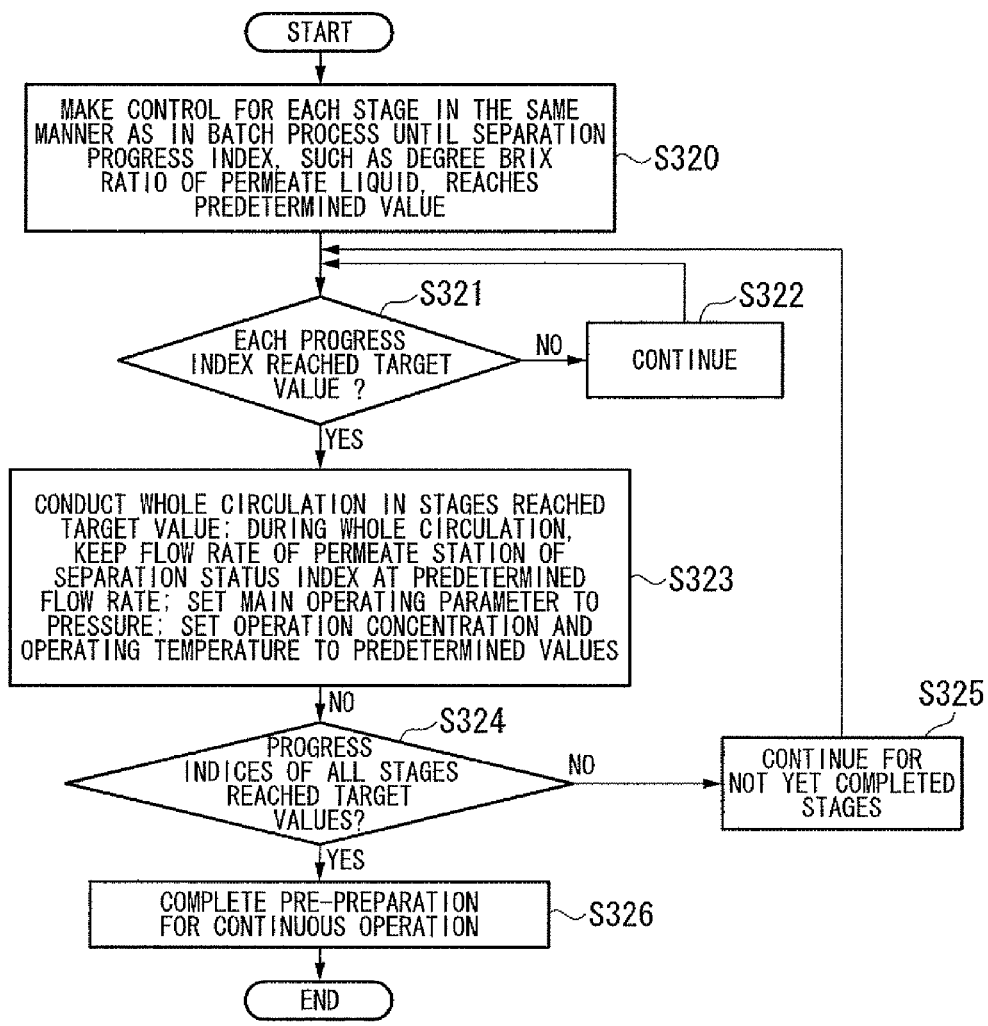
FIG. 17 is a flowchart illustrating control on progress in stages in the separation system shown in FIG. 15.

Next, control on progress of stages in the separation system of FIG. 15 will be described with reference to the flowchart of FIG. 17.

The control is made for each stage in the same manner as in the batch process until the separation progress index, such as the degree Brix ratio of the permeate liquid, reaches a predetermined value (step S320). It is then determined whether or not each of the separation progress index has reached the target value (step S321). If negative in step S321, the measurement results are read out again and the routine proceeds to step S321 (step S322).

If affirmative in step S321, stages with the separation progress index reached the target value is subject to whole circulation. During the whole circulation, the flow rate of the permeate liquid of the separation status index is maintained at a predetermined flow rate. The main operating parameter here is the pressure and the operation concentration and the operating temperature are set to predetermined values (step S323).

And then, it is determined whether or not the progress indices of all of the stages have reached the target values. If negative in the determination, then the operation status is continued (step S325) and the routine proceeds to step S321.

On the other hand, if affirmative in the determination, then the pre-preparation for continuous operation is completed (step S326).

Figure 18:
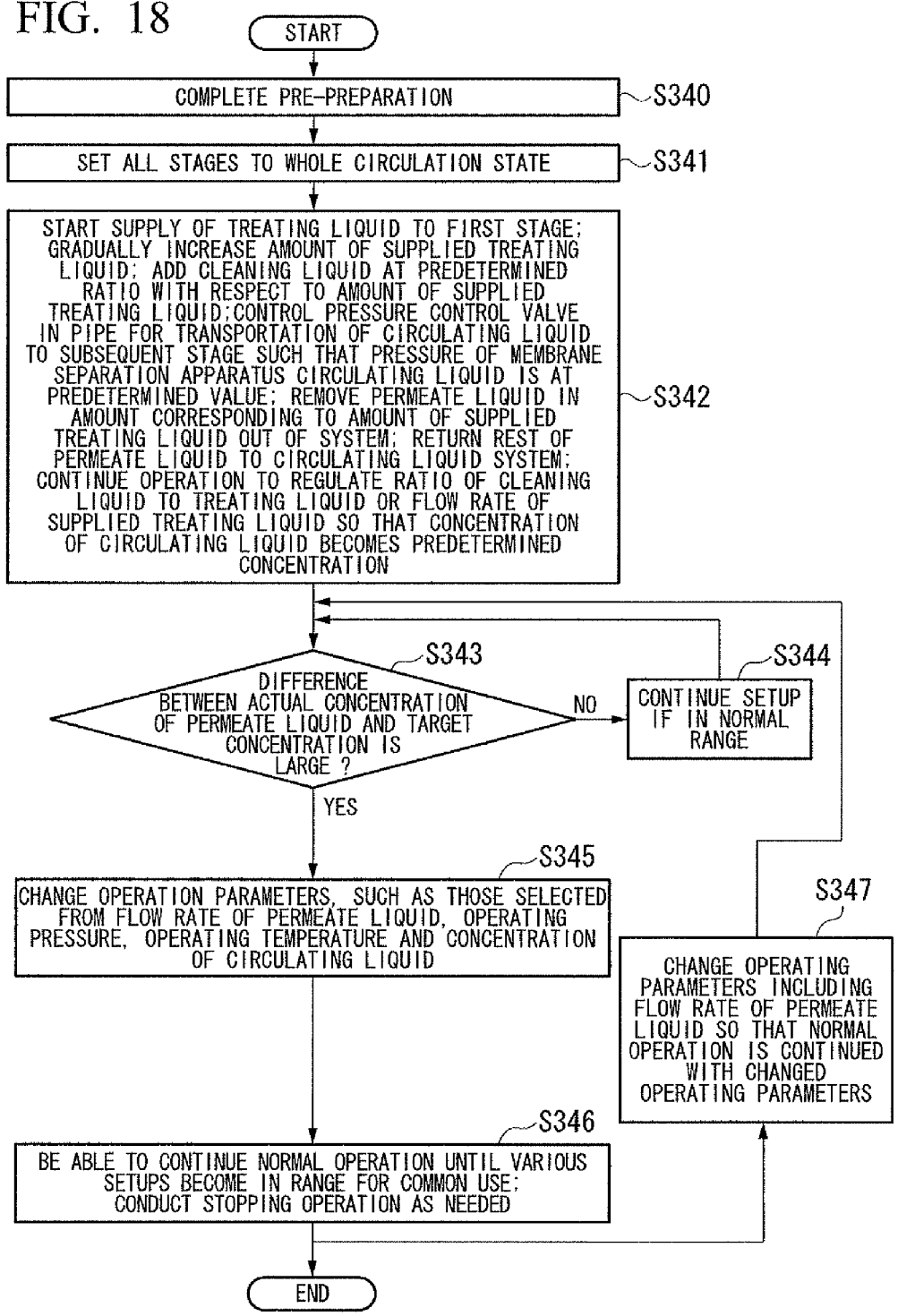
FIG. 18 is a flowchart illustrating an operation of the separation system shown in FIG. 10 during a continuous operation with a flow rate of the permeate liquid as an operating parameter.

Next, an operation of the separation system of FIG. 10 after the continuous operation is started with the flow rate of the permeate liquid as the operating parameter until the continuous operation is stopped will be described with reference to the flowchart of FIG. 18.

Now that the washing water and the permeate liquid may be introduced from either a suction side or a discharge side of the pressure increase pump.

After the pre-preparation is completed (step S340), and all the stages are in the whole circulation state (step S341), supply of the treating liquid is started at the first stage. The amount of the supplied treating liquid is increased gradually. The cleaning liquid is added at a predetermined ratio with respect to the amount of the supplied treating liquid. The pressure control valve in a pipe for transportation of the circulating liquid to the subsequent stage is controlled such that the pressure of the membrane separation apparatus circulating liquid is at the predetermined value. The permeate liquid in an amount corresponding to the amount of the supplied treating liquid is removed out of the system. The rest of the permeate liquid is returned to the circulating liquid system. The operation is continued to regulate the ratio of the cleaning liquid to the treating liquid (cleaning liquid/treating liquid) or the flow rate of the supplied treating liquid so that the concentration of the circulating liquid becomes the predetermined concentration (step S342).

And then, it is determined whether or not difference between the actual concentration of the permeate liquid and the target concentration is larger than a predetermined threshold (step S343). If negative in step S343, that is, difference is within a normal range, the setup is continued (step S344). The routine proceeds to step S343. If affirmative in step S343, operation parameters, such as those selected from the flow rate of the permeate liquid, the operating pressure, the operating temperature the concentration of the circulating liquid and the like are changed (step S345). The normal operation is continued until various setups become in the range in common use. If the normal operation is continued, the operating parameters including the flow rate of the permeate liquid are changed so that the normal operation is continued with the changed operating parameters (step S347). A stopping operation is conducted as needed (step S346).

INDUSTRIAL APPLICABILITY

The separation method according to the present invention is widely applicable to synthesis of polymers and oligomers from small substances including polyglycerin, saccharides and peptide, separation, fractionation, reaction systems and crystallization. The separation is conducted between materials obtained through decomposition of natural or artificial substances, such as polymers, oligomers, resin and plants and unreacted substances, substances that have not completed reaction, intermediate substances, materials and products.

Also, if the material to be processed contains salts, such as sodium chloride, sodium chloride may be removed together with low-molecular glycerin and polyglycerin. As a result, polyglycerin with lower content of salts, such as sodium chloride, may be recovered in the residual liquid. The membrane can be appropriately selected from nanomembranes and ultrafiltration membranes according to the purposes.

Furthermore, In evaluation of a pressure-driven separation membrane or a membrane separation apparatus incorporating the same, substances or components to be processed in membrane separation, a membrane separation apparatus incorporating the same, the separation membrane or the membrane separation apparatus incorporating the same, and a solvent used therefor, a method of evaluating the separation membrane is provided. The evaluation method utilizes a relationship between an index representing permeability, such as in terms of transmittance or a rejection of each substance or component in the mixture, and an index representing permeability, such as in terms of transmittance or a rejection of an arbitrarily selected substance or component.

According to the evaluating method, evaluation of the separation membrane is represented in terms of a comparative relationship with permeability of the substance based on standard substances, and sensitiveness in separating capability of the membrane, i.e., performance of separating mutually similar substances, and the range of the substances to be processed can be represented. Data may be stored as computer programs or as data files of spreadsheet software so as to be able to be used as simulation software. Accumulation of such data can be provided a database useful for selection of membranes.

The invention claimed is:

1. A method of fractionating or isolating a target substance using a membrane, the method comprising: in a diafiltration process including supplying a membrane separation apparatus with a treating liquid containing multiple target substances and extracting a target substance into a permeate liquid supplied from the membrane separation apparatus to fractionate or isolate the target substance from other target substances remaining in a residual liquid, using a separation status index which quantizes a separation state of the membrane separation apparatus in a separating operation and which is used as a target value of the separating operation, and a progress index which quantizes a degree of progress of the separating operation;

controlling an operating parameter such that a measurement value of the separation status index is in a predetermined range of a first set value which is preset as the separation status index before the separating operation based on the separation status index and the progress index of the separating operation;

changing the first set value of the separation status index to a third set value which is preset when a measurement value of the progress index of the separating operation is in a predetermined range of a second set value which is preset as the progress index of the separating operation before the separating operation; and controlling the operating parameter such that a measurement value of the separation status index is in a predetermined range of the third set value in the changing step, wherein:

the separation status index is selected from at least one of a flow rate of the permeate liquid, a saccharide content of the permeate liquid, a saccharide content ratio provided by the saccharide content of permeate liquid being divided by the saccharide content of the circulating liquid, refractive index of the permeate liquid, density of the permeate liquid, and light transmission of the permeate liquid;

the progress index is selected from at least one of an elapsed time of the separation, a cumulative amount of the permeate liquid, a cumulative amount of the supplied cleaning liquid, an amount of the circulating liquid, an amount of a liquid in the circulation tank, separating result index from concentration of the residual liquid, separating result index from concentration of the permeate liquid, separating result index from concentration of the unfiltered liquid, a saccharide content, a viscosity, an electric conductivity, a measurement value, a pH, an analytical value that is based on the selected progress index, and a calculated value that is based on the selected progress index; and the operating parameter is selected from at least one of an operating pressure of the membrane separation apparatus, a temperature of the membrane separation apparatus, a concentration of the circulating liquid, and an amount of the circulating liquid.

2. A method of fractionating or isolating a target substance using the membrane according to claim 1,
wherein multiple or subsequently successive stages of a series of diafiltration processes corresponding to the supply of the treating liquid are provided, and permeability of the target substance is controlled by provided predetermined ranges of the separation status index and/or the operating parameter suitably selected with respect to a progress index for each stage.

3. A method of fractionating or isolating a target substance using the membrane according to claim 2, wherein beginning and completion of each of the stages are determined based on the separation status index and/or the progress index.

4. A method of fractionating or isolating a target substance using the membrane according to claim 1, wherein at least one of an amount of a liquid supplied to the membrane separation apparatus, an amount of a liquid extracted from the system from the membrane separation apparatus or an amount of return liquid into the permeate liquid is controlled based on an index substantially indicating concentration of the circulating liquid or the residual liquid processed in a separation membrane.

5. A method of fractionating or isolating a target substance using the membrane according to claim 1, wherein the separation membrane is a nanomembrane or an ultrafiltration membrane.

6. A method of fractionating or isolating a target substance using the membrane according to claim 1, wherein the separation membrane is a tubular membrane.

7. A method of fractionating or isolating a target substance using the membrane according to claim 1, wherein "a dilute liquid by extraction of a final circulating liquid of a previous batch process" and/or "a reprocessing liquid of a previous batch" and/or "a permeate liquid of a previous batch" are used as an treating liquid, a cleaning liquid or a "recycling liquid" at a batch process subsequent to a batch process in which the liquids are produced.

8. A method of fractionating or isolating a target substance using the membrane according to claim 1, wherein one or more of a reverse osmosis membrane, a nanomembrane and an ultrafiltration membrane is used as the separation membrane.

9. A method of fractionating or isolating a target substance using the membrane according to claim 1, wherein the treating liquid is a mixture liquid containing polyglycerin.

10. A method of fractionating or isolating a target substance using the membrane according to claim 1, wherein the treating liquid is a mixture liquid containing multiple polyglycerins and at least one of glycerin, diglycerin and triglycerin is removed from the mixture liquid.

11. A method of fractionating or isolating a target substance using a membrane according to claim 1, wherein the membrane separation apparatus further comprises:
a unit for monitoring the separation status index and/or the progress index of the separating operation; and
a unit for controlling at least one operating parameter selected from the operating pressure of the membrane separation apparatus, the operating temperature of the membrane separation apparatus, the concentration of the circulating liquid and an amount of the circulating liquid.

12. A method of fractionating or isolating a target substance using a membrane according to claim 11, wherein the membrane separation apparatus further comprises:
a function to determine operating pressure and/or a flow rate of the permeate liquid, based on at least one of concentration of the permeate liquid, degree Brix in the permeate liquid, a cumulative amount of the permeate liquid or elapsed time; and
a regulating function to supply a cleaning liquid while regulating the cleaning liquid to corresponding concentration of the circulating liquid, degree Brix in the circulating liquid or a flow rate of the circulating liquid to perform diafiltration.

13. A method of fractionating or isolating a target substance using a membrane according to claim 1, wherein the measurement values and analytical values provided by a sensor or an analyzing device, or numerically processed values obtained from the measurement values and the progress index of analytical values is used as the separation status index, wherein
the progress index is the elapsed time, the amount of the permeate liquid, or an amount of a cleaning liquid, and the numerically processed value is differential value, average value, or integral value.

* * * * *